(12) United States Patent
Srinivasan et al.

(10) Patent No.: US 8,658,111 B2
(45) Date of Patent: Feb. 25, 2014

(54) DROPLET ACTUATORS, MODIFIED FLUIDS AND METHODS

(75) Inventors: Vijay Srinivasan, Durham, NC (US);
Vamsee Pamula, Durham, NC (US);
Ramakrishna Sista, Morrisville, NC (US); Arjun Sudarsan, Cary, NC (US);
Prasanna Thwar, Los Altos, CA (US)

(73) Assignee: Advanced Liquid Logic, Inc., Morrisville, NC (US)

( * ) Notice: Subject to any disclaimer, the term of this patent is extended or adjusted under 35 U.S.C. 154(b) by 22 days.

(21) Appl. No.: 13/031,760

(22) Filed: Feb. 22, 2011

(65) Prior Publication Data

US 2011/0180571 A1     Jul. 28, 2011

Related U.S. Application Data

(63) Continuation-in-part of application No. 11/639,594, filed on Dec. 15, 2006, and a continuation of application No. PCT/US2009/055139, filed on Aug. 27, 2009.

(60) Provisional application No. 60/745,058, filed on Apr. 18, 2006, provisional application No. 60/745,039, filed on Apr. 18, 2006, provisional application No. 60/745,043, filed on Apr. 18, 2006, provisional application No. 60/745,059, filed on Apr. 18, 2006, provisional application No. 60/745,914, filed on Apr. 28, 2006, provisional application No. 60/745,950, filed on Apr. 28, 2006, provisional application No. 60/746,797, filed on May 9, 2006, provisional application No. 60/746,801, filed on May 9, 2006, provisional application No. 60/806,412, filed on Jun. 30, 2006, provisional application No. 60/807,104, filed on Jul. 12, 2006, provisional application No. 61/092,278, filed on Aug. 27, 2008, provisional application No. 61/094,891, filed on Sep. 6, 2008.

(51) Int. Cl.
*B01L 3/00* (2006.01)
*B01D 57/02* (2006.01)

(52) U.S. Cl.
USPC ........... 422/502; 422/503; 422/504; 204/450; 204/600

(58) Field of Classification Search
USPC ........... 422/502–505; 436/180; 204/450, 600
See application file for complete search history.

(56) References Cited

U.S. PATENT DOCUMENTS 4,390,403 A     6/1983 Batchelder
4,636,785 A     1/1987 Le Pesant (Continued)

FOREIGN PATENT DOCUMENTS

JP    62-222853 A     9/1987
JP    2004249668 A    9/2004

(Continued)

OTHER PUBLICATIONS

Jie Ding, "System level architectural optimization of semi-reconfigurable microfluidic system," M.S. Thesis, Duke University Dept of Electrical Engineering, 2000.

(Continued)

*Primary Examiner* — Brian R Gordon
(74) *Attorney, Agent, or Firm* — William A. Barrett; Ward & Smith, P.A.

(57) ABSTRACT

The present invention provides droplet actuators, modified fluids and methods relating to droplet operations. An aspect includes a droplet actuator including a droplet operations substrate; an oil based filler fluid on the droplet operations substrate comprising an oil soluble additive in the filler fluid; and a droplet in contact with the oil based filler fluid. Still other aspects are provided.

36 Claims, 5 Drawing Sheets

(56) References Cited

U.S. PATENT DOCUMENTS

| | | |
|---|---|---|
| 5,181,016 A | 1/1993 | Lee |
| 5,240,994 A | 8/1993 | Brink et al. |
| 5,486,337 A | 1/1996 | Ohkawa |
| 5,851,769 A | 12/1998 | Gray et al. |
| 5,955,028 A | 9/1999 | Chow |
| 5,980,719 A | 11/1999 | Cherukuri et al. |
| 6,106,685 A | 8/2000 | McBride et al. |
| 6,130,098 A | 10/2000 | Handique et al. |
| 6,294,063 B1 | 9/2001 | Becker et al. |
| 6,319,668 B1 | 11/2001 | Nova et al. |
| 6,379,929 B1 | 4/2002 | Burns et al. |
| 6,432,290 B1 | 8/2002 | Harrison et al. |
| 6,473,492 B2 | 10/2002 | Prins |
| 6,485,913 B1 | 11/2002 | Becker et al. |
| 6,538,823 B2 | 3/2003 | Kroupenkine et al. |
| 6,545,815 B2 | 4/2003 | Kroupenkine et al. |
| 6,565,727 B1 | 5/2003 | Shenderov |
| 6,596,238 B1 | 7/2003 | Belder et al. |
| 6,613,560 B1 | 9/2003 | Tso et al. |
| 6,629,826 B2 | 10/2003 | Yoon et al. |
| 6,665,127 B2 | 12/2003 | Bao et al. |
| 6,761,962 B2 | 7/2004 | Bentsen et al. |
| 6,773,566 B2 | 8/2004 | Shenderov |
| 6,790,011 B1 | 9/2004 | Le Pesant et al. |
| 6,855,881 B2 | 2/2005 | Tanaami |
| 6,911,132 B2 | 6/2005 | Pamula et al. |
| 6,924,792 B1 | 8/2005 | Jessop |
| 6,949,176 B2 | 9/2005 | Vacca et al. |
| 6,958,132 B2 | 10/2005 | Chiou et al. |
| 6,977,033 B2 | 12/2005 | Becker et al. |
| 6,989,234 B2 | 1/2006 | Kolar et al. |
| 6,995,024 B2 | 2/2006 | Smith et al. |
| 7,052,244 B2 | 5/2006 | Fouillet et al. |
| 7,163,612 B2 | 1/2007 | Sterling et al. |
| 7,189,359 B2 | 3/2007 | Yuan et al. |
| 7,211,223 B2 | 5/2007 | Fouillet e |
| 7,211,442 B2 | 5/2007 | Gilbert et al. |
| 7,255,780 B2 | 8/2007 | Shenderov |
| 7,328,979 B2 | 2/2008 | Decre et al. |
| 7,329,545 B2 | 2/2008 | Pamula et al. |
| 7,438,860 B2 | 10/2008 | Takagi et al. |
| 7,439,014 B2 | 10/2008 | Pamula et al. |
| 7,458,661 B2 | 12/2008 | Kim et al. |
| 7,531,072 B2 | 5/2009 | Roux et al. |
| 7,547,380 B2 | 6/2009 | Velev |
| 7,556,776 B2 * | 7/2009 | Fraden et al. .................. 422/504 |
| 7,569,129 B2 | 8/2009 | Pamula et al. |
| 7,641,779 B2 | 1/2010 | Becker et al. |
| 7,727,466 B2 | 6/2010 | Meathrel et al. |
| 7,727,723 B2 | 6/2010 | Pollack et al. |
| 7,759,132 B2 | 7/2010 | Pollack et al. |
| 7,763,471 B2 | 7/2010 | Pamula et al. |
| 7,767,147 B2 * | 8/2010 | Adachi et al. .................. 422/63 |
| 7,767,435 B2 | 8/2010 | Chiu et al. |
| 7,815,871 B2 | 10/2010 | Pamula et al. |
| 7,816,121 B2 | 10/2010 | Pollack et al. |
| 7,822,510 B2 | 10/2010 | Paik et al. |
| 7,851,184 B2 | 12/2010 | Pollack et al. |
| 7,875,160 B2 | 1/2011 | Jary |
| 7,901,947 B2 | 3/2011 | Pollack et al. |
| 7,919,330 B2 | 4/2011 | de Guzman et al. |
| 7,922,886 B2 | 4/2011 | Fouillet et al. |
| 7,939,021 B2 | 5/2011 | Smith et al. |
| 7,943,030 B2 | 5/2011 | Shenderov |
| 7,989,056 B2 | 8/2011 | Plissonnier et al. |
| 7,998,436 B2 | 8/2011 | Pollack |
| 8,007,739 B2 | 8/2011 | Pollack et al. |
| 8,041,463 B2 | 10/2011 | Pollack et al. |
| 8,048,628 B2 | 11/2011 | Pollack et al. |
| 8,075,754 B2 | 12/2011 | Sauter-Starace et al. |
| 8,088,578 B2 | 1/2012 | Hua et al. |
| 8,093,064 B2 | 1/2012 | Shah et al. |
| 8,137,917 B2 | 3/2012 | Pollack et al. |
| 8,147,668 B2 | 4/2012 | Pollack et al. |
| 8,202,686 B2 | 6/2012 | Pamula et al. |
| 8,208,146 B2 | 6/2012 | Srinivasan et al. |
| 8,221,605 B2 | 7/2012 | Pollack et al. |
| 8,236,156 B2 | 8/2012 | Sarrut et al. |
| 8,268,246 B2 | 9/2012 | Srinivasan et al. |
| 8,287,711 B2 | 10/2012 | Pollack et al. |
| 8,304,253 B2 | 11/2012 | Yi et al. |
| 8,317,990 B2 | 11/2012 | Pamula et al. |
| 8,342,207 B2 | 1/2013 | Raccurt et al. |
| 8,349,276 B2 | 1/2013 | Pamula et al. |
| 8,364,315 B2 | 1/2013 | Sturmer et al. |
| 8,388,909 B2 | 3/2013 | Pollack et al. |
| 8,389,297 B2 | 3/2013 | Pamula et al. |
| 8,394,249 B2 | 3/2013 | Pollack et al. |
| 8,426,213 B2 | 4/2013 | Eckhardt et al. |
| 8,440,392 B2 | 5/2013 | Pamula et al. |
| 8,444,836 B2 | 5/2013 | Fouillet et al. |
| 2002/0005354 A1 | 1/2002 | Spence et al. |
| 2002/0036139 A1 | 3/2002 | Becker et al. |
| 2002/0043463 A1 | 4/2002 | Shenderov |
| 2002/0058332 A1 | 5/2002 | Quake et al. |
| 2002/0093651 A1 | 7/2002 | Roe |
| 2002/0125135 A1 | 9/2002 | Derand et al. |
| 2002/0128546 A1 | 9/2002 | Silver |
| 2002/0143437 A1 | 10/2002 | Handique et al. |
| 2002/0168671 A1 | 11/2002 | Burns et al. |
| 2002/0172969 A1 | 11/2002 | Burns et al. |
| 2003/0006140 A1 | 1/2003 | Vacca et al. |
| 2003/0007898 A1 | 1/2003 | Bohm et al. |
| 2003/0012483 A1 | 1/2003 | Ticknor et al. |
| 2003/0012699 A1 | 1/2003 | Moore et al. |
| 2003/0049177 A1 | 3/2003 | Smith et al. |
| 2003/0082081 A1 | 5/2003 | Fouillet et al. |
| 2003/0103021 A1 | 6/2003 | Young et al. |
| 2003/0119057 A1 | 6/2003 | Gascoyne et al. |
| 2003/0164295 A1 | 9/2003 | Sterling |
| 2003/0183525 A1 | 10/2003 | Elrod et al. |
| 2003/0205632 A1 | 11/2003 | Kim et al. |
| 2003/0206351 A1 | 11/2003 | Kroupenkine |
| 2003/0224528 A1 | 12/2003 | Chiou et al. |
| 2003/0227100 A1 | 12/2003 | Chandross et al. |
| 2004/0007377 A1 | 1/2004 | Fouillet et al. |
| 2004/0031688 A1 | 2/2004 | Shenderov |
| 2004/0042721 A1 | 3/2004 | Kroupenkine et al. |
| 2004/0055536 A1 | 3/2004 | Kolar et al. |
| 2004/0055891 A1 | 3/2004 | Pamula et al. |
| 2004/0058450 A1 | 3/2004 | Pamula et al. |
| 2004/0091392 A1 | 5/2004 | McBridge et al. |
| 2004/0101445 A1 | 5/2004 | Shivets et al. |
| 2004/0136876 A1 | 7/2004 | Fouillet et al. |
| 2004/0141884 A1 | 7/2004 | Unno et al. |
| 2004/0231987 A1 | 11/2004 | Sterling et al. |
| 2005/0048581 A1 | 3/2005 | Chiu et al. |
| 2005/0056569 A1 | 3/2005 | Yuan et al. |
| 2005/0100675 A1 | 5/2005 | Mao et al. |
| 2005/0158755 A1 | 7/2005 | Lee et al. |
| 2005/0179746 A1 | 8/2005 | Roux et al. |
| 2005/0227264 A1 | 10/2005 | Nobile et al. |
| 2005/0287572 A1 | 12/2005 | Mathies et al. |
| 2006/0021875 A1 | 2/2006 | Griffith et al. |
| 2006/0039823 A1 | 2/2006 | Yamakawa et al. |
| 2006/0054503 A1 | 3/2006 | Pamula et al. |
| 2006/0068450 A1 | 3/2006 | Combette et al. |
| 2006/0092239 A1 | 5/2006 | Sung et al. |
| 2006/0164490 A1 | 7/2006 | Kim et al. |
| 2006/0194331 A1 | 8/2006 | Pamula et al. |
| 2006/0210443 A1 | 9/2006 | Stearns et al. |
| 2006/0231398 A1 | 10/2006 | Sarrut et al. |
| 2007/0023292 A1 | 2/2007 | Kim et al. |
| 2007/0037294 A1 | 2/2007 | Pamula et al. |
| 2007/0045117 A1 | 3/2007 | Pamula et al. |
| 2007/0064990 A1 | 3/2007 | Roth |
| 2007/0086927 A1 | 4/2007 | Natarajan et al. |
| 2007/0207513 A1 | 9/2007 | Sorensen et al. |
| 2007/0217956 A1 | 9/2007 | Pamula et al. |
| 2007/0241068 A1 | 10/2007 | Pamula et al. |
| 2007/0242105 A1 | 10/2007 | Srinivasan |

| Publication No. | Date | Inventor |
|---|---|---|
| 2007/0242111 A1 | 10/2007 | Pamula et al. |
| 2007/0243634 A1 | 10/2007 | Pamula et al. |
| 2007/0267294 A1 | 11/2007 | Shenderov |
| 2007/0275415 A1 | 11/2007 | Srinivasan et al. |
| 2008/0003142 A1 | 1/2008 | Link et al. |
| 2008/0006535 A1 | 1/2008 | Paik et al. |
| 2008/0038810 A1 | 2/2008 | Pollack et al. |
| 2008/0044893 A1 | 2/2008 | Pollack et al. |
| 2008/0044914 A1 | 2/2008 | Pamula |
| 2008/0050834 A1 | 2/2008 | Pamula et al. |
| 2008/0053205 A1 | 3/2008 | Pollack et al. |
| 2008/0091848 A1 | 4/2008 | Kuo et al. |
| 2008/0105549 A1 | 5/2008 | Pamela et al. |
| 2008/0124252 A1 | 5/2008 | Marchand et al. |
| 2008/0142376 A1 | 6/2008 | Fouillet et al. |
| 2008/0151240 A1 | 6/2008 | Roth |
| 2008/0210558 A1 | 9/2008 | Sauter-Starace et al. |
| 2008/0247920 A1 | 10/2008 | Pollack et al. |
| 2008/0264797 A1 | 10/2008 | Pamula et al. |
| 2008/0274513 A1 | 11/2008 | Shenderov |
| 2008/0281471 A1 | 11/2008 | Smith et al. |
| 2008/0283414 A1 | 11/2008 | Monroe et al. |
| 2008/0302431 A1 | 12/2008 | Marchand et al. |
| 2008/0305481 A1 | 12/2008 | Whitman et al. |
| 2009/0014394 A1 | 1/2009 | Yi et al. |
| 2009/0042319 A1 | 2/2009 | De Guzman et al. |
| 2009/0127123 A1 | 5/2009 | Raccurt et al. |
| 2009/0134027 A1 | 5/2009 | Jary |
| 2009/0142564 A1 | 6/2009 | Plissonnier et al. |
| 2009/0155902 A1 | 6/2009 | Pollack et al. |
| 2009/0192044 A1 | 7/2009 | Fouillet et al. |
| 2009/0260988 A1 | 10/2009 | Pamula et al. |
| 2009/0263834 A1 | 10/2009 | Sista et al. |
| 2009/0280251 A1 | 11/2009 | De Guzman et al. |
| 2009/0280475 A1 | 11/2009 | Pollack et al. |
| 2009/0280476 A1 | 11/2009 | Srinivasan et al. |
| 2009/0283407 A1 | 11/2009 | Shah et al. |
| 2009/0288710 A1 | 11/2009 | Viovy et al. |
| 2009/0291433 A1 | 11/2009 | Pollack et al. |
| 2009/0304944 A1 | 12/2009 | Sudarsan et al. |
| 2009/0311713 A1 | 12/2009 | Pollack et al. |
| 2009/0321262 A1 | 12/2009 | Adachi et al. |
| 2010/0025242 A1 | 2/2010 | Pamula et al. |
| 2010/0025250 A1 | 2/2010 | Pamula et al. |
| 2010/0028920 A1 | 2/2010 | Eckhardt |
| 2010/0032293 A1 | 2/2010 | Pollack et al. |
| 2010/0041086 A1 | 2/2010 | Pamula et al. |
| 2010/0048410 A1 | 2/2010 | Shenderov et al. |
| 2010/0062508 A1 | 3/2010 | Pamula et al. |
| 2010/0068764 A1 | 3/2010 | Sista et al. |
| 2010/0087012 A1 | 4/2010 | Shenderov et al. |
| 2010/0096266 A1 | 4/2010 | Kim et al. |
| 2010/0116640 A1 | 5/2010 | Pamula et al. |
| 2010/0118307 A1 | 5/2010 | Srinivasan et al. |
| 2010/0120130 A1 | 5/2010 | Srinivasan et al. |
| 2010/0126860 A1 | 5/2010 | Srinivasan et al. |
| 2010/0130369 A1 | 5/2010 | Shenderov et al. |
| 2010/0140093 A1 | 6/2010 | Pamula et al. |
| 2010/0143963 A1 | 6/2010 | Pollack |
| 2010/0151439 A1 | 6/2010 | Pamula et al. |
| 2010/0190263 A1 | 7/2010 | Srinivasan et al. |
| 2010/0194408 A1 | 8/2010 | Sturmer et al. |
| 2010/0221713 A1 | 9/2010 | Pollack et al. |
| 2010/0236927 A1 | 9/2010 | Pope et al. |
| 2010/0236928 A1 | 9/2010 | Srinivasan et al. |
| 2010/0236929 A1 | 9/2010 | Pollack et al. |
| 2010/0258441 A1 | 10/2010 | Sista et al. |
| 2010/0279374 A1 | 11/2010 | Sista et al. |
| 2010/0320088 A1 | 12/2010 | Fouillet et al. |
| 2010/0323405 A1 | 12/2010 | Pollack et al. |
| 2011/0076692 A1 | 3/2011 | Sista et al. |
| 2011/0104816 A1 | 5/2011 | Pollack et al. |
| 2011/0118132 A1 | 5/2011 | Winger et al. |
| 2011/0177586 A1* | 7/2011 | Ismagilov et al. ......... 435/287.2 |
| 2011/0209998 A1 | 9/2011 | Shenderov |
| 2011/0213499 A1 | 9/2011 | Sturmer et al. |
| 2011/0303542 A1 | 12/2011 | Srinivasan et al. |
| 2012/0132528 A1 | 5/2012 | Shenderov et al. |
| 2012/0165238 A1 | 6/2012 | Pamula et al. |
| 2012/0276544 A1* | 11/2012 | Quake et al. ................. 435/6.12 |

FOREIGN PATENT DOCUMENTS

| | | |
|---|---|---|
| JP | 2005219231 A | 8/2005 |
| JP | 2008093566 A | 4/2008 |
| WO | WO9915876 A1 | 4/1999 |
| WO | WO9917093 A1 | 4/1999 |
| WO | WO9954730 A1 | 10/1999 |
| WO | 200069565 A1 | 11/2000 |
| WO | 2000073655 A1 | 12/2000 |
| WO | WO03069380 A1 | 8/2003 |
| WO | 2004029585 A1 | 4/2004 |
| WO | 2004030820 | 4/2004 |
| WO | WO2004027490 A1 | 4/2004 |
| WO | 2005047696 A1 | 5/2005 |
| WO | 2006013303 A1 | 2/2006 |
| WO | WO2006026351 A1 | 3/2006 |
| WO | 2006070162 A1 | 7/2006 |
| WO | 2006081558 | 8/2006 |
| WO | 2006127451 A2 | 11/2006 |
| WO | WO 2006124458 A2 | 11/2006 |
| WO | 2006134307 A1 | 12/2006 |
| WO | 2006138543 | 12/2006 |
| WO | 2007003720 A1 | 1/2007 |
| WO | 2007012638 A1 | 2/2007 |
| WO | 2007033990 A1 | 3/2007 |
| WO | 2007048111 | 4/2007 |
| WO | 2007120240 A2 | 10/2007 |
| WO | 2007120241 A2 | 10/2007 |
| WO | 20070120241 | 10/2007 |
| WO | 2007123908 A2 | 11/2007 |
| WO | 2008051310 | 5/2008 |
| WO | 2008055256 | 5/2008 |
| WO | 2008068229 A1 | 6/2008 |
| WO | 2008091848 A2 | 7/2008 |
| WO | 20080098236 | 8/2008 |
| WO | 20080101194 | 8/2008 |
| WO | WO 2008098236 A1 | 8/2008 |
| WO | WO2008098236 A2 | 8/2008 |
| WO | 2008106678 A1 | 9/2008 |
| WO | 2008109664 A1 | 9/2008 |
| WO | 2008112856 | 9/2008 |
| WO | 2008116209 A1 | 9/2008 |
| WO | 2008116221 A1 | 9/2008 |
| WO | 2008118831 A2 | 10/2008 |
| WO | 2008124846 A2 | 10/2008 |
| WO | 2008131420 A2 | 10/2008 |
| WO | 20080134153 | 11/2008 |
| WO | 2009002920 A1 | 12/2008 |
| WO | 20090003184 | 12/2008 |
| WO | 2009011952 A1 | 1/2009 |
| WO | 2009021173 A1 | 2/2009 |
| WO | 2009021233 A2 | 2/2009 |
| WO | 2009026339 A2 | 2/2009 |
| WO | 20090021173 | 2/2009 |
| WO | 2009029561 A2 | 3/2009 |
| WO | 2009032863 A2 | 3/2009 |
| WO | 2009052095 A1 | 4/2009 |
| WO | 2009052123 A2 | 4/2009 |
| WO | 2009052321 A2 | 4/2009 |
| WO | 2009052345 | 4/2009 |
| WO | 2009052348 A2 | 4/2009 |
| WO | 2009076414 | 6/2009 |
| WO | 2009086403 A2 | 7/2009 |
| WO | 2009111769 A2 | 9/2009 |
| WO | 2009135205 A2 | 11/2009 |
| WO | 2009137415 A2 | 11/2009 |
| WO | 2009140373 A2 | 11/2009 |
| WO | 2009140671 A2 | 11/2009 |
| WO | 2010004014 A1 | 1/2010 |
| WO | 2010006166 A2 | 1/2010 |
| WO | 2010009463 A2 | 1/2010 |
| WO | 2010019782 A2 | 2/2010 |
| WO | 20100027894 | 3/2010 |
| WO | 2010042637 A2 | 4/2010 |
| WO | 2010077859 A3 | 7/2010 |

(56) References Cited

FOREIGN PATENT DOCUMENTS

OTHER PUBLICATIONS

Moon, Hyejin, Ph.D., "Electrowetting-on-dielectric microfluidics: Modeling, physics, and MALDI application," University of California, Los Angeles, 2006.

T. Taniguchi et al., "Chemical reactions in microdroplets by electrostatic manipulation of droplets in liquid media," Lab on a Chip, vol. 2, No. 2, pp. 19-23 (2002).

Dewey A, Srinivasan V, Icoz E, "Visual modeling and design of microelectromechanical system transducers", Microelectronics Journal, vol. 32, pp. 373-381, Apr. 2001.

Dewey A, Srinivasan V, Icoz E, "Towards a visual modeling approach to designing micro electromechanical system transducers," Journal of Micromechanics and Microengineering, vol. 9, pp. 332-340, Dec. 1999.

R.B. Fair, A. Khlystov, T. Tailor, V. Ivanov, R.D. Evans, V. Srinivasan, V. Pamula, M.G. Pollack, P.B. Griffin, and J. Zhoud, "Chemical and Biological Applications of Digital Microfluidic Devices", IEEE Design and Test of Computers, vol. 24(1): pp. 10-24 Jan.-Feb. 2007.

R.B. Fair, A. Khlystov, V. Srinivasan, V. K. Pamula, K.N. Weaver, "Integrated chemical/biochemical sample collection, pre-concentration, and analysis on a digital microfluidic lab-on-a-chip platform," Lab-on-a-Chip: Platforms, Devices, and Applications, Conf. 5591, SPIE Optics East, Philadelphia, Oct. 25-28, 2004.

R.B. Fair, V. Srinivasan, V.K. Pamula, and K.N. Weaver, "Bead-Based and Solution-Based Assays Performed on a Digital Microfluidic Platform," Biomedical Engineering Society (BMES) Fall Meeting, Baltimore, MD, Oct. 1, 2005.

R.B. Fair, V. Srinivasan, H. Ren, P. Paik, V.K. Pamula, M.G. Pollack, "Electrowetting-based On-Chip Sample Processing for Integrated Microfluidics," IEEE Inter. Electron Devices Meeting (IEDM), pp. 32.5.1-32.5.4, 2003.

Phil Paik, Vamsee K. Pamula, and K. Chakrabarty, "Thermal effects on Droplet Transport in Digital Microfluidics with Applications to Chip Cooling Processing for Integrated Microfluidics," International Conference on Thermal, Mechanics, and Thermomechanical Phenomena in Electronic Systems (ITherm), pp. 649-654, 2004.

Phil Paik, Vamsee K. Pamula, and Richard B. Fair, "Rapid droplet mixers for digital microfluidic systems," Lab on a Chip, vol. 3, pp. 253-259, 2003.

Phil Paik, Vamsee K. Pamula, Michael G. Pollack and Richard B. Fair, "Electrowetting-based droplet mixers for microfluidic systems", Lab on a Chip (LOC), vol. 3, pp. 28-33, 2003.

Vamsee K. Pamula and Krishnendu Chakrabarty, "Cooling of integrated circuits using droplet-based microfluidics," Proc. ACM Great Lakes Symposium on VLSI, pp. 84-87, Apr. 2003.

V.K. Pamula, V. Srinivasan, H. Chakrapani, R.B. Fair, E.J. Toone, "A droplet-based lab-on-a-chip for colorimetric detection of nitroaromatic explosives," Proceedings of Micro Electro Mechanical Systems, pp. 722-725, 2005.

M. G. Pollack, P. Y. Paik, A. D. Shenderov, V. K. Pamula, F. S. Dietrich, and R. B. Fair, "Investigation of electrowetting-based microfluidics for real-time PCR applications," µTAS 2003.

Pollack et al., "Electrowetting-Based Microfluidics for High-Throughput Screening," smallTalk2001 Conference Program Abstract (Aug. 2001), p. 149, San Diego.

Hong Ren, Vijay Srinivasan, Michael G. Pollack, and Richard B. Fair, "Automated electrowetting-based droplet dispensing with good reproducibility," Proc. Micro Total Analysis Systems (mTAS), pp. 993-996, 2003.

Hong Ren, Vijay Srinivasan, and Richard B. Fair, "Design and testing of an interpolating mixing architecture for electrowetting-based droplet-on-chip chemical dilution", Transducers 2003, pp. 619-622, 2003.

Vijay Srinivasan, Vamsee K. Pamula, Richard B. Fair, "An integrated digital microfluidic lab-on-a-chip for clinical diagnostics on human physiological fluids," Lab on a Chip, vol. 4, pp. 310-315, 2004.

Vijay Srinivasan, Vamsee K. Pamula, Richard B. Fair, "Droplet-based microfluidic lab-on-a-chip for glucose detection," Analytica Chimica Acta, vol. 507, No. 1, pp. 145-150, 2004.

V. Srinivasan, V.K. Pamula, P. Paik, and R.B. Fair, "Protein Stamping for MALDI Mass Spectrometry Using an Electrowetting-based Microfluidic Platform," Lab-on-a-Chip: Platforms, Devices, and Applications, Conf. 5591, SPIE Optics East, Philadelphia, Oct. 25-28, 2004.

Vijay Srinivasan, Vamsee K. Pamula, Michael G. Pollack, and Richard B. Fair, "Clinical diagnostics on human whole blood, plasma, serum, urine, saliva, sweat, and tears on a digital microfluidic platform," Proc. Micro Total Analysis Systems (mTAS), pp. 1287-1290, 2003.

Vijay Srinivasan, Vamsee K. Pamula, Michael G. Pollack, and Richard B. Fair, "A digital microfluidic biosensor for multianalyte detection", Proc. IEEE 16th Micro Electro Mechanical Systems Conference, pp. 327-330, 2003.

Vijay Srinivasan, Vamsee K. Pamula, K. Divakar Rao, Michael G. Pollack, Joseph A. Izatt, and Richard B. Fair, "3-D imaging of moving droplets for microfluidics using optical coherence tomography," Proc. Micro Total Analysis Systems (mTAS), pp. 1303-1306, 2003.

F. Su, S. Ozev and K. Chakrabarty, "Testing of droplet-based microelectrofluidic systems", Proc. IEEE International Test Conference, pp. 1192-1200, 2003.

Nicole Weaver, "Application of Magnetic Microspheres for Pyrosequencing on a Digital Microfluidic Platform", Aug. 2005.

Vijay Srinivasan, Anand Jog and Richard B. Fair, "Scalable Macromodels for Microelectromechanical Systems", Technical Proc. 2001 Int. Conf. on Modeling and Simulation of Microsystems, pp. 72-75, 2004.

"Making materials fit the future: accommodating relentless technological requirements means researchers must recreated and reconfigure materials, frequently challenging established laws of physics, while keeping an eye on Moore's law", R&D Magazine, Dec. 2001.

"Lab-on-a-Chip Technology May Present New ESD Challenges", Electrostatic Discharge Journal, Mar. 2002.

"Laboratory on a Chip", Popular Mechanics, Mar. 2002.

"Chip Juggles Droplets", Technology Research News, Sep. 4-11, 2002.

"Chip mixes droplets faster", MIT Technology Review, Oct. 2003.

Rival et al.,"Towards Single Cells Gene Expression on EWOD Lab on Chip," ESONN 2008, Aug. 26, 2008, Grenoble, France; Abstract in Proceedings, Poster presented at conference.

Rival et al., "Towards single cells gene expression preparation and analysis on ewod lab on chip," Nanobio Europe 2009; Abstract in Proceedings, Poster distributed at conference.

Rival et al., "EWOD Digital Microfluidic Device for Single Cells Sample Preparation and Gene Expression Analysis," Lab Automation 2010, Palm Springs Convention Center, Palm Springs, CA, USA, Jan. 23-27, 2010; Abstract in Proceedings, Poster distributed at conference.

Sudarsan et al., "Prinled Circuit Technology for Fabrication of Plastic-Based Microfluidic Devices," Anal. Chem. vol. 76, pp. 3229-3235. 2004.

Wang et al., "Comparison of enzyme activities for Pompe, Fabry, and Gaucher diseases on CDC's Quality Control spots between microplate fluorometry, mass spectrometry, and digital microfluidic fluorometry," APHL Newborn Screening and Genetic Testing Symposium, San Diego, 2011.

Wang et al., "Efficient in-droplet separation of magnetic particles for digital microfluidics," J. Micromech. Microeng. 17 (2007) 2148-2156.

Zeng et al, "Actuation and Control of Droplets by Using Electrowetting-on-Dielectric," Chin. Phys. Lett. vol. 21, No. 9, pp. 1851-1854, 2004.

Burton et al.,"Diagnosis of Fabry and Gaucher diseases from the Pilot Screening of Newborns for Lysosomal Storage Disorders in Illinois," APHL Newborn Screening and Genetic Testing Symposium, San Diego, 2011.

Bali et al.,"Comparison of Methods for the Analysis of Lysosomal Enzyme Activities in Quality Control Dried Blood Spot Specimens," LSD World Meeting, Orlando, FL, 2013.

(56) References Cited

OTHER PUBLICATIONS

Delattre et al.,"Macro to microfluidics system for biological environmental monitoring." Biosensors and Bioelectronics, vol. 36, Issue 1, Jun.-Jul. 2012, pp. 230-235.
Eckhardt et al.,"Development and validation of a single-step fluorometric assay for Hunter syndrome," APHL Newborn Screening and Genetic Testing Symposium, San Diego, 2011.
Graham et al., "Development of Quality Control Spots for Lysosomal Storage Disorders under cGMP," APHL Newborn Screening and Genetic Testing Symposium, San Diego, 2011.
Pamula et al., "Cooling of Integrated Circuits Using Droplet-Based Microfluids," Proc. ACM Great Lakes Symposium on VLSI, pp. 84-87, 2003.
Ren et al., "Design and Testing of an Interpolating Mixing Architecture for Electrowetting-Based Droplet-on-Chip Chemical Dilution," Transducers, pp. 619-622, 2003.
Rival et al., "New insight on droplet dynamics under electrowetting actuation and design tools for speeding up product development," 8th Electrowetting Workshop, Athens, Greece, 2012.
Sista et al., "Digital Microfluidic Platform for Multiplexing Enzyme Assays: Implications for Lysosomal Storage Disease Screening in Newborns," Clinical Chemistry, vol. 57, pp. 1444-1451, 2011.
Sista et al., "Performance of a digital microfluidic assay for Gaucher and Hurler disorders," APHL Newborn Screening and Genetic Testing Symposium, San Diego, 2011.
Shi et al, "Evaluation of stability of fluorometric reagent kits for screening of Lysosomal Storage Disorders," APHL Newborn Screening and Genetic Testing Symposium, San Diego, 2011.
Srinivasan et al., "Feasibility of a point of care newborn screening platform for hyperbilirubinemia," APHL Newborn Screening and Genetic Testing Symposium, San Diego, 2011.
Boles et al., "Droplet-Based Pyrosequencing Using Digital Microfluidics," Analytical Chemistry, vol. 83, pp. 8439-8447, Sep. 2011.
Dewey et al., "Towards a Visual Modeling Approach to Designing Microelectromechanicai System Transducers," Journal of Micromechanics and Microengineering, vol. 9, pp. 332-340, Dec. 1999.
Dewey et al, "Visual Modeling and Design of Microelectromechanical System Transducers," Microelectronics Journal, vol. 32, pp. 373-381, Apr. 2001.
Fair et al., "A Microwatt Metal Insulator Solution Transport (MIST) Device for Scalable Digital Biomicrofluidic Systems," IEEE IEDM Technical Digest, pp. 16.4.1-16.4.4, 2001.
Fair et al., "Electrowetting-Based On-Chip Sample Processing for Integrated Microfluidics," IEEE Int'l Electron Devices Meeting (IEDM), 2003.
Fair et al., "Integrated Chemical/Biochemical Sample Collection. Pre-Concentration, and Analysis on a Digital Microfluidic Lab-on-a-Chip Platform," Lab-on-a-Chip: Platforms, Devices, and Applications, Conf. 5591, SPIE Optics East, Philadelphia, Oct. 25-28, 2004.
Fair et al., "Bead-Based and Solution-Based Assays Performed on a Digital Microfluidic Platform," Biomedical Engineering Society (BMES) Fall Meeting, Baltimore, MD, Oct. 1, 2005.
Fair et al., "Chemical and Biological Applications of Digital Microfluidic Devices," IEEE Design and Test of Computers, vol. 24(1): pp. 10-24, Jan.-Feb. 2007.
Hua et al., "Multiplexed Real-Time Polymerase Chain Reaction on a Digital Microfluidic Platform," Analytical Chemistry. vol. 82, pp. 2310-2316, Mar. 2010.
Millington et al., "Digital Microfluidics: A Future Technology in the Newborn Screening Laboratory?," Seminars in Perinatology, vol. 34, pp. 163-169, Apr. 2010.
Paik et al., "Rapid Droplet Mixers for Digital Microfluidic Systems," Lab on a Chip, vol. 3, pp. 253-259, 2003. (More mixing videos available, along with the article, at LOC's website.).
Paik et al., "Electrowetting-Based Droplet Mixers for Microfluidic Systems," Lab on a Chip (LOC), vol. 3, pp. 28-33, 2003 (more mixing videos available, along with the article, at LOC's website).
Paik et al., "Thermal Effects on Droplet Transport in Digital Microfluidics with Applications to Chip Cooling Processing for Integrated Miorofluidics," Int'l Conf. on Thermal, Mechanics, and Thermomechanical Phenomena in Electronic systems (ITherm), pp. 649-654, 2004.
Paik et al., "Coplanar Digital Microfluidics Using Standard Printed Circuit Board Processes," 9th Int'l Conf. on Miniaturized Systems for Chemistry and Life Sciences, Boston, MA, pp. 566-568, Oct. 9-13, 2005.
Paik et al., "Droplet-Based Hot Spot Cooling Using Topless Digital Microfluidics on a Printed Circuit Board," Int'l Workshops on Thermal Investigations of ICs and Systems (Thermic), pp. 278-283, 2005.
Paik et al., "Adaptive Hot-Spot Cooling of Integrated Circuits Using Digital Microfluidics ," ASME Int'l Mechanical Engineering Congress and Exposition (IMECE), Nov. 5-11, 2005.
Paik et al., "Programmable Flow-Through Real-Time PCR Using Digital Microfluidics," 11th Int'l Conf. on Miniaturized Systems for Chemistry and Life Sciences, Paris, France, pp. 1559-1581, Oct. 7-11, 2007.
Paik et al, "Adaptive Cooling of Integrated Circuits Using Digital Microfluidics," accepted for publication in IEEE Transactions on VLSI Systems, 2007, and Artech House, Norwood, MA, 2007.
Paik et al., "A Digital-Microfluidic Approach to Chip Cooling," IEEE Design & Test of Computers, vol. 25, pp. 372-381, Jul. 2008.
Pamula et al., "Microfluidic Electrowetting-Based Droplet Mixing," Proceedings, MEMS Conf. Berkeley, pp. 8-10, Aug. 2001.
Pamula et al., "Cooling of Integrated Circuits Using Droplet-Based Microfluidics," Proc. ACM Great Lakes Symposium on VLSI, pp. 84-87, 2003.
Pamula et al., "A Droplet-Based Lab-on-a-Chip for Colorimetric Detection of Nitroaromatic Explosives," Proceedings of Micro Electra Mechanical Systems, pp. 722-725, 2005.
Pollack et al., "Electrowetting-Based Actuation of Liquid Droplets for Microfluidic Applications," Applied Physics Letters, vol. 77, No. 11, pp. 1725-1726, Sep. 11, 2000.
Pollack, M.G., "Electrowelting-Based Miaoactuation of Droplets for Digital Microfluidics," Ph.D. Thesis, Department of Electrical and Computer Engineering, Duke University, 2001.
Pollack et al, "Electrowetting-Based Microfluidics for High-Throughput Screening," SmallTalk 2001 Conf. Program Abstract, p. 149, San Diego, Aug. 2001.
Pollack et al, "Electrowetting-Based Actuation of Droplets for Integrated Microfludics," Lab on a Chip (LOC), vol. 2, pp. 96-101, 2002.
Pollack et al., "Investigation of Electrowetting-Based Microfluidics for Real-Time PCR Applications," 7th Int'l Conf. on Micro Total Analysis Systems (μTAS), 2003.
Pollack et al., "Applications of Electrowetting-Based Digital Microfluidics in Clinical Diagnostics," Expert Rev. Mol. Diagn., vol. 11(4), pp. 393-407, 2011.
Punnamaraju et al., "Voltage Control of Droplet Interface Bilayer Lipid Membrane Dimensions," Langmuir The Acs Journal of Surfaces and Colloids, vol. 27, Issue 2, pp. 618-626, 2011.
Ren et al "Dynamics of Electro-Wetting Droplet Transport," Sensors and Actuators B (Chemical), vol. B87, No. 1,201-6, 2002.
Ren et al., "Micro/Nano Liter Droplet Formation and Dispensing by Capaotanoe Metering and Electrowetting Actuation," IEEE-NANO, pp. 369-372, 2002.
Ren et al., "Automated Electrowetting-Based Droplet Dispensing with Good Reproducibility," Proc. Micro Total Analysis Systems (μTAS), pp. 993-996, 2003.
Sista, R., "Development of a Digital Microfluidic Lab-on-a-Chip for Automated Immunoassay with Magnetically Responsive Beads," Ph.D. Thesis, Dep't of Chemical Engineering, Florida State University, 2007.
Sista et al., "Heterogeneous Immunoassays Using Magnetic Beads on a Digital Microfluidic Platform," Lab on a Chip, vol. 8, pp. 2188-2196, Dec. 2008.
Sista et al., "Digital Microfluidic Platform for Multiplexing Enzyme Assays: Implications for Lysosomal Storage Disease Screening in Newborns," Clinical Chemistry, vol. 57, pp. 1444-1451,2011.
Sista et al., "Rapid, Single-Step Assay for Hunter Syndrome in Dried Blood Spots Using Digital Microfluidics," Clinica Chimica Acta, vol. 412, pp. 1895-1897, 2011.

(56) References Cited

OTHER PUBLICATIONS

Srinivasan et al., "Scalable Macromodels for Microelekctromechanical Systems," Technical Proc. 2001 Int'l Conf. on Modeling and Simulation of Microsystems, pp. 72-75, 2001.

Srinivasan et al., "A Digital Microfluidic Biosensor for Multianalyte Detection," Proc. IEEE 16th Annual Int'l Conf. on Micro Electro Mechanical Systems. pp. 327-330, 2003.

Srinivasan et al., "Clinical Diagnostics on Human Whole Blood, Plasma, Serum, Urine, Saliva, Sweat, and Tears on a Digital Microfluidic Platform," Proc. Micro Total Analysis Systems (μTAS), pp. 1287-1290, 2003.

Srinivasan et al., "3-D Imaging of Moving Droplets for Microfluidics Using Optical Coherence Tomography," Micro Total Analysis Systems (μTAS), pp. 1303-1306, 2003.

Srinivasan et al., "Droplet-Based Microfluidic Lab-on-a-Chip for Glucose Detection," Analytica Chimica Acta, vol. 507, No. 1, pp. 145-150, 2004.

Srinivasan et al., "An Integrated Digital Microfluidic Lab-on-a-Chip for Clinical Diagnostics on Human Physiological Fluids," Lab on a Chip, vol. 4, pp. 310-315, 2004.

Srinivasan et al., "Protein Stamping for MALDI Mass Spectrometry Using an Electrowetting-Based Microfluidic Platform," Lab-on-a-Chip: Platforms, Devices, and Applications, Conf, 5591, SPIE Optics East, Philadelphia, Oct. 25-28, 2004.

Srinivasan, V.. "A Digital Microfluidic Lab-on-a-Chip for Clinical Diagnostic Applications," Ph.D. thesis, Dep't of Electrical and Computer Engineering, Duke University, 2005.

Su et al., "Yield Enhancement of Digital Microfluidics-Based Biochips Using Space Redundancy and Local Reconfiguration," Proc. Design, Automation and Test in Europe (DATE) Conf., pp, 1198-1201, 2005.

Bottausci et al., "Fully Integrated EWOD Based Bio-Analysis Device," Labautomation 2011, Palm Springs Convention Center, Palm Springs, CA, USA, Jan. 29-Feb. 2, 2011,Abstract in Proceedings on line, Poster distributed at conference.

Delattre et al., "Towards an industrial fabrication process for electrowetting chip using standard MEMS Technology," μTAS2008, San Diego; Abstract in Proceedings, Poster presented at conference.

Delattre et al., "SmartDrop," Forum 4I 2009, Grenoble, France, May 14, 2009; Flyer distributed.

Delattre et al., "SmartDrop: An integrated system from sample preparation to analysis using real-time PCR, 10th International Symposium on Protection against Chemical and Biological Warfare Agents," Jun. 8-11, 2010, Stockholm, Swesen; Abstract and paper in Proceedings, Presentation presented at conference, Poster distributed at conference.

Delapierre et al., "SmartDrop: An Integrated System from Sample Collection to Result using real-time PCR," 4th National Bio-Threat Conference, Dec. 7-9, 2010, New Orleans, LA, USA; Abstract in Proceedings, Poster presented at conference.

Jary et al., Development of complete analytical system for Environment and homeland security, 14th Biodetection Technologies Conference, Jun. 25-26, 2009, Baltimore, US; Abstract in Proceedings, Poster presented at conference.

Marchand et al., "Organic Synthesis in Soft Wall-Free Microreactors: Real-Time Monitoring of Fluorogenic Reactions," Analytical Chemistry vol. 80, pp. 6051-6055, 2008.

Tolun et al., "A Novel Fluorometric Enzyme Analysis Method for Hunter Syndrome Using Dried Blood Spots," Mol. Genet. Metab. (2012), doi:10.1016/j.ymgme.2001.12.011.

Wulff-Burchfield et al., "Microfluidic Platform Versus Conventional Real-Time Polymerase Chain Reaction for the Detection of Mycolplasma pneumoniae in Respiratory Specimens," Dignostic Microbiology and Infectious Disease, 2010, vol. 67, pp. 22-29.

Xu et al., "Digital Microfluidic Biochip Design for Protein Crystallization," IEEE-NIH, 2007.

Yi et al., "Soft Printing of Droplets Digitized by Electrowetting," 12th Int'l Conf. on Solid State Sensors, Actuators and Microsystems, Boston, Jun. 8-12, 2003, pp. 1804-1807.

Yi et al, "Geometric Surface Modification of Nozzles for Complete Transfer of Liquid Drops," Solid-State Sensor, Actuators and Microsystems Workshop, Hilton Head Island, South Carolina, Jun. 6-10, 2004, pp. 164-167.

Yi et al., "Characterization of Electrowetting Acutation on Addressable Single-Side Coplanar Electrodes," J. Micromesh. Microeng. 2006, vol. 16, pp. 2053-2059, http://dx.doi.org/10.1088/0960-1317/16/10/018.

Yi et al., "Soft Printing of Droplets Pre-Metered by Electrowetting," Sensors and Actuators, vol. 114, pp. 347-354, 2004.

Yi et al., "EWOD Actuation with Electrode-Free Cover Plate," The 13th International Conference on Solid-State Sensors, Actuators and Microsystems, Seoul, Korea, Jun. 5-9, 2005.

Zhao et al., "Microparticle Concentration and Separation byTraveling-Wave Dielectrophoresis (twfDEP) for Digital Microfiuidics," J. Microelectromechanical Systems, vol. 6, No. 6, pp. 1472-1481, Dec. 2007.

Zhao et al, "Droplet Manipulation and Microparticle Sampling on Perforated Microfilter Membranes," J. Micromesh. Microeng., vol. 18, 2008, pp. 1-11.

Chakrabarty, , "Automated Design of Microfluidics-Based Biochips: connecting Biochemistry of Electronics CAD", IEEE International Conference on Computer Design, San Jose, CA, Oct. 1-4, 2006, 93-100.

Chakrabarty, et al., "Design Automation Challenges for Microfluidics-Based Biochips", DTIP of MEMS & MOEMS, Montreux, Switzerland, Jun. 1-3, 2005.

Cotten, et al., "Digital Microfluidics: a novel platform for multiplexed detection of lysosomal storage diseases", Abstract #3747.9. Pediatric Academic Society Conference, 2008.

Emani, et al., "Novel Microfluidic Platform for Point of Care Hypercoagulability Panel Testing", Circulation, vol. 122, 2010, A14693.

Fair, , "Biomedical Applications of Electrowetting Systems", 5th International Electrowetting Workshop, Rochester, NY, 2006.

Fouillet, et al., "Design and Validation of a Complex Generic Fluidic Microprocessor Based on EWOD Droplet for Biological Applications", 9th International Conference on Miniaturized Systems for Chem and Life Sciences, Boston, MA, Oct. 9-13, 2005, 58-60.

Hua, et al., "Rapid Detection of Methicilliin-Resistant Staphylococcus Aureus (MRSA) Using Digital Microfluidics", Proc. μTAS, 2008.

Millington, et al., "Digital Microfluidics: a Novel Platform for Multiplexing Assays Used in Newborn Screening", Proceedings of the 7th International and Latin American Congress. Oral Presentations. Rev Invest Clin; vol. 61 (Supt. 1), 2009, 21-33.

Pamula, et al., "Digital microfluidic lab-on-a-chip for protein crystallization", 5th Protein Structure Initiative "Bottlenecks" Workshop, Nih, Bethesda, Md, Apr. 13-14, 2006,1-16.

Pamula, et al., "Digital Microfluidic Methods in Diagnosis of Neonatal Biochemical Abnormalities", Developing Safe and Effective Devices and Instruments for Use in the Neonatal Intensive Care for the 21st Century, Pediatric Academic Societies' Annual Meeting, Vancouver, Canada, 2010.

Pamula, et al., "Digital Microfluidic Platform for Multiplexing Lsd Assays in Newborn Screening", Lsd World Meeting, Las Vegas, Nv, Feb 16-18, 2011.

Pamula, et al., "Digital Microfluidics Platform for Lab-on-a-chip applications", Duke University Annual Post Doctoral Research Day, 2002.

Punnamaraju, "Voltage and Photo Induced Effects in Droplet-Interface-Bilayer Lipid", PhD Thesis, University of Cincinnati, 2011.

Ren, et al., "Automated on-chip droplet dispensing with vol. control by electrowetting actuation and capacitance metering", Sensors and Actuators B: Chemical, vol. 98, Mar. 2004, 319-327.

Ren, et al., "Design and testing of an interpolating mixing architecture for electrowettingbased droplet-on-chip chemical dilution", Transducers, 12th International Conference on Solid- State Sensors, Actuators and Microsystems, 2003, 619-622.

Rouse, et al., "Digital microfluidics: a novel platform for multiplexing assays used in newborn screening", Poster 47, 41st Aacc's Annual Oak Ridge Conference Abstracts, Clinical Chemistry, vol. 55, 2009, 1891.

(56) References Cited

OTHER PUBLICATIONS

Schell, et al., "Evaluation of a Digital Microfluidic real-time Pcr Platform to detect Dna of Candida albicans", Eur. J. Clin Microbiol Infect Dis, Published on-line Doi 10.1007/s10096-012-15616, Feb. 2012.

Sista, et al., "96-Immunoassay Digital Microfluidic Multiwell Plate", Proc. pTAS, 2008,.

Sista, et al., "Development of a digital microfluidic platform for point of care testing", Lab on a chip, vol. 8, Dec. 2008, First published as an Advance Article on the web, 5 Nov. 2008, 2091-2104.

Sista, et al., "Digital Microfluidic platform for multiplexing Lsd assays in newborn screening", Aphl Newborn Screening and Genetic Testing Symposium, Orlando, 2010,.

Srinivasan, et al., "Digital Microfluidics: a novel platform for multiplexed detection of lysosomal storage diseases for newborn screening", Aacc Oak Ridge Conference Abstracts, Clinical Chemistry, vol. 54, 2008, 1934.

Srinivasan, et al., "Electrowetting", Chapter 5, Methods in Bioengineering: Biomicrofabrication and Biomicrofluidics, Ed. J.D. Zahn, Isbn: 9781596934009, Artech House Publishers, 2010,.

Srinivasan, et al., "Low cost digital microfluidic platform for protein crystallization", Enabling Technologies for Structural Biology, Nigms Workshop, Bethesda, Md., Mar. 4-6, 2009, J-23.

Thwar, et al., "Dna sequencing using digital microfluidics", Poster 42, 41st Aacc's Annual Oak Ridge Conference Abstracts, Clinical Chemistry vol. 55, 2009, 1891.

Tolun, et al., "Dried blood spot based enzyme assays for lysosomal storage disorders", 2011 Tokyo Meeting on Lysosomal Storage Disease Screening, Tokyo, Aug. 5, 2011.

Wang, et al., "Efficient in-droplet separation of magnetic particles for digital microfluidics", Journal of Micromechanics and Microengineering, vol. 17, 2007, 21482156.

Xu, et al., "A Cross-Referencing-Based Droplet Manipulation Method for HighThroughput and Pin-Constrained Digital Microfluidic Arrays", Proceedings of conference on Design, Automation and Test in Europe (Date ), Apr. 2007.

Xu, et al., "Automated, Accurate and Inexpensive Solution-Preparation on a Digital Microfluidic Biochip", Proc. IEEE Biomedical Circuits and Systems Conference (BioCAS), 2008, 301-304.

Xu, et al., "Defect-Tolerant Design and Optimization of a Digital Microfluidic Biochip for Protein Crystallization", IEEE Transactions on Computer Aided Design, vol. 29, No. 4, 2010, 552-565.

Xu, et al., "Design and Optimization of a Digital Microfluidic Biochip for Protein Crystallization", Proc. IEEE/Acm International Conference on Computer-Aided Design (Iccad), Nov. 2008, 297-301.

et al., "Digital Microfluidic Biochip Design for Protein Crystallization", IEEE-Nih Life Science Systems and Applications Workshop, Lisa, Bethesda, Md, Nov 8-9, 2007, 140- 143.

Xu, et al., "Integrated Droplet Routing in the Synthesis of Microfluidic Biochips", IEEE, 2007, 948-953.

Xu, et al., "Parallel Scan-Like Test and Multiple-Defect Diagnosis for Digital Microfluidic Biochips", IEEE Transactions on Biomedical Circuits and Systems, vol. 1(2), Jun. 2007, 148-158.

Xu, et al., "Parallel Scan-Like Testing and Fault Diagnosis Techniques for Digital Microfluidic Biochips", Proceedings of the 12th IEEE European Test Symposium (Ets), Freiburg, Germany, May 20-24, 2007, 63-68.

Yi, et al., "Characterization of electrowetting actuation on addressable single-side coplanar electrodes", Journal of Micromechanics and Microengineering, vol. 16.,Oct. 2006 http://dx.doi.org/10.1088/0960-1317/16/10/018, published online at stacks.iop.org/Jmm/16/2053, 25 Aug. 2006, 2053-2059.

Yi, et al., "Geometric surface modification of nozzles for complete transfer of liquid drops", Solid-State Sensor, Actuator and Microsystems Workshop, Hilton Head Island, South Carolina, Jun. 6-10, 2004, 164-167.

Zhao, et al., "Synchronization of Concurrently-Implemented Fluidic Operations in Pin-Constrained Digital Microfluidic Biochips", Vlsi Design, (Best Paper Award), 2010,.

\* cited by examiner

DROPLET ACTUATORS, MODIFIED FLUIDS AND METHODS

1 RELATED APPLICATIONS

This application is a continuation-in-part of and incorporates by reference U.S. patent application Ser. No. 11/639,594, entitled "Filler Fluids for Droplet Operations" filed on Dec. 15, 2006, the application of which claims priority to and incorporates by reference related provisional U.S. Patent Application Nos. 60/745,058, entitled "Filler Fluids for Droplet-Based Microfluidics" filed on Apr. 18, 2006; 60/745,039, entitled "Apparatus and Methods for Droplet-Based Blood Chemistry," filed on Apr. 18, 2006; 60/745,043, entitled "Apparatus and Methods for Droplet-Based PCR," filed on Apr. 18, 2006; 60/745,059, entitled "Apparatus and Methods for Droplet-Based Immunoassay," filed on Apr. 18, 2006; 60/745,914, entitled "Apparatus and Method for Manipulating Droplets with a Predetermined Number of Cells" filed on Apr. 28, 2006; 60/745,950, entitled "Apparatus and Methods of Sample Preparation for a Droplet Microactuator," filed on Apr. 28, 2006; 60/746,797 entitled "Portable Analyzer Using Droplet-Based Microfluidics," filed on May 9, 2006; 60/746,801, entitled "Apparatus and Methods for Droplet-Based Immuno-PCR," filed on May 9, 2006; 60/806,412, entitled "Systems and Methods for Droplet Microactuator Operations," filed on Jun. 30, 2006; and 60/807,104, entitled "Method and Apparatus for Droplet-Based Nucleic Acid Amplification," filed on Jul. 12, 2006

In addition to the patent applications cited above, this application is a continuation of and incorporates by reference International Patent Application No. PCT/US2009/055139, entitled "Droplet Actuators, Modified Fluids And Methods" International filing date of Aug. 27, 2009, the application of which claims priority to and incorporates by reference related U.S. Provisional Patent Application Nos. 61/092,278, filed on Aug. 27, 2008, entitled "Droplet Actuators, Modified Fluids and Methods," and 61/094,891, filed on Sep. 6, 2008, entitled "Droplet Actuators, Modified Fluids and Methods".

In addition to the patent applications cited above, this application relates to and incorporates by reference the entire disclosure of International Patent Application No. PCT/US2008/072604, entitled "Use of Additives for Enhancing Droplet Actuation," International filing date of Aug. 8, 2008; U.S. provisional Patent Application No. 60/980,620, entitled "Use of Additives for Enhancing Droplet Actuation," filed on Oct. 17, 2007; and U.S. provisional Patent Application No. 60/954,587, entitled "Use of Additives for Enhancing Droplet Actuation," filed on Aug. 8, 2007.

2 FIELD OF THE INVENTION

The present invention generally relates to the field of conducting droplet operations in a droplet actuator. In particular, the present invention is directed to droplet actuator designs and droplet actuator fluid compositions for enhancing droplet operations.

3 BACKGROUND OF THE INVENTION

Droplet actuators are used to conduct a wide variety of droplet operations. A droplet actuator typically includes two substrates separated by a gap. The substrates include electrodes for conducting droplet operations. The space is typically filled with a filler fluid that is immiscible with the fluid that is to be manipulated on the droplet actuator, so that the droplet actuator includes a droplet phase in the form of a droplet at least partially bounded by a filler fluid phase consisting of the filler fluid. The formation and movement of the droplet phase droplets is controlled by electrodes, which can be employed to conduct a variety of droplet operations. Because different droplet phase fluids and droplet operations often require differences in filler fluid properties, and vice versa, there is a need for new droplet actuator designs and droplet actuator fluid compositions for enhancing droplet operations.

4 BRIEF DESCRIPTION OF THE INVENTION

The present invention is directed to droplet actuators, modified fluids and methods.

In one embodiment, a droplet actuator is provided comprising a substrate comprising electrodes arranged for conducting droplet operations on a droplet operations surface of the substrate; a filler fluid phase in contact with the droplet operations surface at least partially surrounding a droplet phase comprising a droplet arranged on one or more of the electrodes, the filler fluid phase being divided by one or more physical barriers into zones; and an opening in the one or more physical barriers for transporting the droplet phase from one zone to another.

In another embodiment, a droplet actuator is provided comprising a droplet operations substrate; an oil based filler fluid on the droplet operations substrate; and a droplet in contact with the oil based filler fluid forming an oil-droplet interface, the droplet comprising an aqueous soluble additive that has a hydrophile-lipophile balance (HLB) in the range of about 10 to about 20.

In yet another embodiment, a droplet actuator is provided comprising a droplet operations substrate; an oil based filler fluid on the droplet operations substrate; and a droplet in contact with the oil based filler fluid forming an oil-droplet interface, the droplet comprising an aqueous soluble additive and water soluble particles that do not bind to a significant quantity of a target substance.

In a further embodiment, a droplet actuator is provided comprising a droplet operations substrate; an oil based filler fluid on the droplet operations substrate comprising an oil soluble additive in the filler fluid; and a droplet in contact with the oil based filler fluid.

5 DEFINITIONS

As used herein, the following terms have the meanings indicated.

"Adsorption" is the loss of substances from the droplet phase to solid surfaces of the droplet actuator.

"Activate" with reference to one or more electrodes means effecting a change in the electrical state of the one or more electrodes which results in a droplet operation.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator or otherwise configured with respect to a droplet actuator in a manner which permits a droplet on the droplet actuator to be brought into contact with the bead, on the droplet actuator and/or off the droplet actuator. Beads may be manufactured using a wide variety of materials, including for example, resins, and polymers. The beads may be any suitable size, including for example, microbeads, microparticles, nano-beads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay reagent. Examples of suitable magnetically responsive beads are described in U.S. Patent Publication No. 2005-0260686, entitled, "Multiplex flow assays preferably with magnetic particles as solid phase," published on Nov. 24, 2005, the entire disclosure of which is incorporated herein by reference for its teaching concerning magnetically responsive materials and beads. The fluids may include one or more magnetically responsive and/or non-magnetically responsive beads. Examples of droplet actuator techniques for immobilizing magnetic beads and/or non-magnetic beads and/or conducting droplet operations protocols using beads are described in U.S. patent application Ser. No. 11/639,566, entitled "Droplet-Based Particle Sorting," filed on Dec. 15, 2006; U.S. patent application Ser. No. 61/039,183, entitled "Multiplexing Bead Detection in a Single Droplet," filed on Mar. 25, 2008; U.S. patent application Ser. No. 61/047,789, entitled "Droplet Actuator Devices and Droplet Operations Using Beads," filed on Apr. 25, 2008; U.S. patent application Ser. No. 61/086,183, entitled "Droplet Actuator Devices and Methods for Manipulating Beads," filed on Aug. 5, 2008; International Patent Application No. PCT/US2008/053545, entitled "Droplet Actuator Devices and Methods Employing Magnetic Beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference.

"Carryover" occurs when substances that are lost from the droplet phase via, for example, adsorption and/or partitioning, make their way into another droplet phase (e.g., from one droplet phase droplet to another droplet phase droplet), resulting in droplet phase cross-contamination.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator.

"Droplet Actuator" means a device for manipulating droplets. For examples of droplets, see U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000, both to Shenderov et al.; Pollack et al., International Patent Application No. PCT/US2006/047486, entitled "Droplet-Based Biochemistry," filed on Dec. 11, 2006, the disclosures of which are incorporated herein by reference. Methods of the invention may be executed using droplet actuator systems, e.g., as described in International Patent Application No. PCT/US2007/009379, entitled "Droplet manipulation systems," filed on May 9, 2007. In various embodiments, the manipulation of droplets by a droplet actuator may be electrode mediated, e.g., electrowetting mediated or dielectrophoresis mediated.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; condensing a droplet from a vapor; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to size of the resulting droplets (i.e., the size of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. In various embodiments, the droplet operations may be electrode mediated, e.g., electrowetting mediated or dielectrophoresis mediated.

"Filler fluid" means a fluid associated with a droplet operations substrate of a droplet actuator, which fluid is sufficiently immiscible with a droplet phase to render the droplet phase subject to electrode-mediated droplet operations. The filler fluid may, for example, be a low-viscosity oil, such as silicone oil. Other examples of filler fluids are provided in International Patent Application No. PCT/US2006/047486, entitled, "Droplet-Based Biochemistry," filed on Dec. 11, 2006; and in International Patent Application No. PCT/US2008/072604, entitled "Use of additives for enhancing droplet actuation," filed on Aug. 8, 2008.

"Immobilize" with respect to magnetically responsive beads, means that the beads are substantially restrained in position in a droplet or in filler fluid on a droplet actuator. For example, in one embodiment, immobilized beads are sufficiently restrained in position to permit execution of a splitting operation on a droplet, yielding one droplet with substantially all of the beads and one droplet substantially lacking in the beads.

"Magnetically responsive" means responsive to a magnetic field at a field strength suitable for substantially immobilizing beads on a droplet actuator. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, CoO, NiO, $Mn_2O_3$, $Cr_2O_3$, and CoMnP. "Magnetically responsive" means not significantly responsive to a magnetic field at a field strength suitable for immobilizing beads on a droplet actuator.

"Partitioning" is the transfer of substances from the droplet phase to the filler fluid phase.

"Target" substances are those substances which are usefully retained in the droplet phase, e.g., because they are analytes or reagents involved in the chemical or biochemical reactions for which the droplet actuator is intended, or because they are waste products that could contaminate the filler fluid phase.

"Washing" with respect to washing a magnetically responsive bead means reducing the amount and/or concentration of one or more substances in contact with the magnetically responsive bead or exposed to the magnetically responsive bead from a droplet in contact with the magnetically responsive bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Other embodiments are described elsewhere herein, and still others will be immediately apparent in view of the present disclosure.

Except where otherwise indicated, the terms "top" and "bottom" are used throughout the description with reference to the top and bottom substrates of the droplet actuator for convenience only, since the droplet actuator is functional regardless of its position in space.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

Large molecular weights are generally about 1000 mw or higher. Small molecular weights are generally less than 1000. Long chains are 50 carbons (for hydrocarbons) or longer or 50 silicons (silicone based) or longer. Short chains are generally less than 50.

6 BRIEF DESCRIPTION OF THE DRAWINGS

7 DETAILED DESCRIPTION OF THE INVENTION

Figure 1:
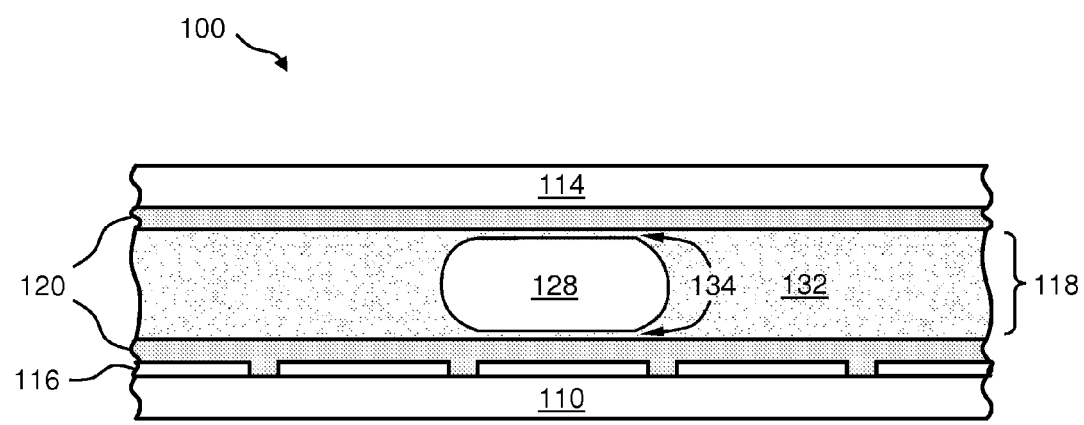
FIG. 1 illustrates a side view of a portion of a droplet actuator, showing an oil film between the droplet and the surfaces of the droplet actuator.

The invention provides modified droplet actuators, improved fluids for use on droplet actuators, droplet actuators including the improved fluids, and methods of conducting droplet operations using the improved fluids and/or modified droplet actuators. Droplet actuators typically employ a droplet phase (e.g., reagents, samples, etc.) and a filler fluid phase (e.g., filler fluids). The invention provides modified fluids for use in one or both of these phases. The modifications of the invention have a variety of improved attributes relative to existing fluids. For example, in certain embodiments, the modified fluids reduce (relative to corresponding fluids lacking the modifications described herein) or minimize or substantially eliminate loss of target substances from the hydrophilic phase due, for example, to the effects of adsorption and/or partitioning of target substances. Further, in certain embodiments, the modified fluids reduce (relative to corresponding fluids lacking the modifications described herein) or minimize or substantially eliminate carryover of target substances. The improved target substance retention is achieved without substantial reduction in the capability of the droplets to be subjected to one or more droplet operations on a droplet actuator of the invention.

In one embodiment, the invention provides droplet phase and filler fluid phase fluids including certain additives. The additives may improve retention of target substances in the droplet phase and/or improve droplet operations. Further, the invention provides droplet actuators including the modified droplet phase and/or filler fluid phase fluids of the invention. The invention also provides methods of conducting droplet operations using such modified droplet phase and/or filler fluid phase fluids of the invention, which methods exhibit improved retention of target substances in the droplet phase and/or improved droplet operations relative to corresponding fluids lacking the additives described herein.

As will be discussed in more detail in the ensuing sections, the invention exhibits advantages including, but not limited to: (1) reducing adsorption, such as by adding an additive to the droplet phase and/or filler fluid phase in order to render one or more target components less likely to adsorb to surfaces of the droplet actuator, (2) reducing partitioning, such as by adding an additive to the droplet phase and/or filler fluid phase in order to reduce the partitioning of one or more target components into the filler fluid phase, (3) reducing carryover, such as by adding an additive to the droplet phase and/or filler fluid phase in order to reduce the carryover of one or more target components from one droplet phase to another droplet phase, and (4) improve one or more droplet operations relative to droplet actuators lacking the modifications and/or improved fluids; and (5) any combinations of (1), (2), (3) and (4).

The invention also provides modified droplet actuators, fluids and methods for maintaining oil film stability in a droplet actuator. The maintenance of the oil film between the droplet and the surface of the droplet actuator is an important factor in optimum operation of the droplet actuator. A stabilized oil film leads to less contamination, such as contamination due to absorption and resorption. In addition, maintenance of the oil film provides for more direct electrowetting and allows for the use of lower voltages for droplet operations.

7.1 Aqueous-Soluble Additives

The invention may include providing an aqueous soluble additive in a droplet phase on a droplet actuator. In one example, the additive includes an aqueous soluble substance that has a hydrophile-lipophile balance (HLB) in the range of about 10 to about 20. In another example, the additive includes an aqueous soluble substance that has a hydrophile-lipophile balance (HLB) in the range of about 11 to about 20. In another example, the additive includes an aqueous soluble substance that has a hydrophile-lipophile balance (HLB) in the range of about 12 to about 20. In another example, the additive includes an aqueous soluble substance that has a hydrophile-lipophile balance (HLB) in the range of about 13 to about 20. In another example, the additive includes an aqueous soluble substance that has a hydrophile-lipophile balance (HLB) in the range of about 14 to about 20. In another example, the additive includes an aqueous soluble substance that has a hydrophile-lipophile balance (HLB) in the range of about 15 to about 20.

Examples of suitable additives include, but are not limited to, polysorbate 20, which is commercially available as Tween® 20, and Triton X-100. Tween® 20 may be supplied by, for example, Pierce Biotechnology, Inc. (Woburn, Mass.). Triton® X-100 may be supplied by, for example, Rohm & Haas Co (Philadelphia, Pa.).

The aqueous-soluble additive may selected and provided in an amount sufficient to interfere with adsorption, partitioning and/or carryover to the extent that the adsorption, partitioning and/or carryover is reduced relative to the adsorption, partitioning and/or carryover of the component in the absence of the additive. The aqueous-soluble additive may selected and provided in an amount sufficient to enhance a droplet operation relative to a corresponding droplet actuator system lacking the additive.

In one embodiment when additive includes Tween® 20. The concentration of Tween® 20 in the droplet phase may, for example, be in the range of from about 001% to about 0.2% by volume, or from about 0.005% to about 0.1% by volume, or from about 0.01% to about 0.08% by volume.

In one embodiment, additive includes Triton X-100. The concentration of Triton X-100 in the droplet phase may, for example, be in the range of from about 0.001% to about 0.2% by volume, or from about 0.005% to about 0.1% by volume, or from about 0.01% to about 0.08% by volume.

In another example, the additive may be an organic solvent, such as dimethyl sulfoxide (DMSO) supplied by Gaylord Chemical Corporation (Slidell, La.). The concentration of DMSO in the droplet phase may, for example, be in the range of from about 0.01% to about 5% by volume, or from about 0.1% to about 2% by volume, or from about 0.5% to about 1% by volume.

A variety of additives may be added to the droplet phase to improve droplet operations by increasing solubility of the target. Examples include 1,3-propanediol; 1,4-butanediol; 1,5-pentanediol; 2,2,2-trifluoroethanol; 2-propanol; 3-mercaptopropionic acid; acetic acid; butyl chloride; chloroform (with ethanol, e.g., 1% ethanol); diethylene glycol; dimethyl sulfoxide; dimethylformamide; ethanol; ethylene glycol; formamide; formic acid; glycerol; isoamyl alcohol; mercaptoethanol; methanol; N,N-dimethlyformamide; N-methlyacetamide; phenol; pyridine; triethanolamine; triethylene glycol; and trifluoroacetic acid. Preferred organic solvent additives are those in which the target has a solubility which is greater than about 10 mg/mL.

Still other suitable additives include partially fluorinated surfactants, such as 1H,1H,2H,2H-perfluoro-1-decanol and 1H,1H,2H,2H-perfluoro-1-octanol; as well as perfluorinated surfactants, such as perfluorodecanoic acid and perfluorododecanoic acid.

An important class of additives for use in the droplet fluid phase is aqueous soluble fluorinated surfactants. A list of fluorinated surfactants is available in Chapter 1 "Fluorinated Surfactants and Repellents" By Erik Kissa, Published by CRC Press, 2001, the entire disclosure of which is incorporated herein by reference. Other suitable fluorinated surfactants are described in Michael Terrazas & Rudi Dams, "A new generation of fluorosurfactants," Speciality Chemicals Magazine, March 2004, vol 24 no 3, the entire disclosure of which is incorporated herein by reference.

Combinations of any of the foregoing surfactants may be used as filler fluid phase additives in accordance with the invention. Further, combinations of organic solvents, as well as combinations of any water miscible solvents with water may also be used in accordance with the invention. Moreover, combinations of foregoing surfactants and organic solvent additives may be used.

The invention also provides a droplet actuator, such as droplet actuator 200, having one or more aqueous droplets including one or more additives selected and provided in an amount which reduces the loss of target substances due to adsorption and/or partitioning. The invention also includes a method of conducting a droplet operation during which operation the droplet includes one or more additives selected and provided in an amount that reduces the loss of target substances due to adsorption and/or partitioning.

In some cases, the surfactant molecules in the aqueous droplets tend to diffuse to the interface of the droplet causing a decrease in the oil-water interfacial tension over time. In some embodiments, it may be useful to diffuse surfactant molecules through the bulk of the droplet phase or otherwise reduce accumulation of the surfactant molecules at the droplet phase/filler fluid phase interface. One solution to this issue involves including water soluble particles, such as polystyrene particles, in the droplet phase. The particles are provided in an amount that enhances mixing within the droplet or otherwise reduces accumulation of surfactant molecules at the interface. In one embodiment, beads, such as polystyrene particles, are selected which tend to migrate to the oil-water interface, thereby reducing accumulation of surfactants at the interface keeping the surfactant within the aqueous phase.

7.2 Oil Soluble Additives

In addition to, or as an alternative to, the water soluble additives described above, certain oil soluble additives may be useful in the filler fluid phase for reducing loss of target droplet phase components from the droplet phase and/or for improving droplet operations. Examples of suitable additives include nonionic low HLB (hydrophile-lipophile balance) surfactants. The HLB is preferably less than about 10 or less than about 5. Suitable examples include: Triton X-15 (HLB=4.9); Span 85 (HLB 1.8); Span 65 (2.1); Span 83 (3.7); Span 80 (4.3); Span 60 (4.7); and fluorinated surfactants.

For example, oil-soluble filler fluid additives may include Span-85 (sorbitan trioleate) and/or Triton® X-15. Span-85 may be supplied by, for example, Merck Schuchardt OHG (Germany). Triton® X-15 may be supplied by, for example, Rohm & Haas Co (Philadelphia, Pa.).

Filler fluid additives are preferably selected and provided in an amount which (1) enables the droplet actuator to conduct or repeat more droplet operations compared to corresponding droplet actuator without the additives; and/or (2) enables one or more droplet operations on the droplet actuator that are not possible on a corresponding droplet actuator without the additives; and/or (3) makes one or more droplet operations more reliable on the droplet actuator as compared to corresponding droplet actuator without the additives; and/ or (4) results in less loss of target substance from the droplet phase during droplet operations as compared to a corresponding droplet operations in the absence of the additives.

In a related example, surfactant(s) are selected and provided in an amount which makes one or more droplet operations possible or more reliable for droplets including one or more specific reagents or mixtures on the droplet actuator as compared to droplet operations for the same droplets including one or more specific reagents or mixtures on a corresponding droplet actuator without the surfactant(s). In another related example, surfactant(s) are selected and provided in an amount which makes one or more droplet operations possible or more reliable for one or more droplets including amphiphilic molecules on the droplet actuator as compared to droplet operations for the same droplets including amphiphilic molecules on a corresponding droplet actuator without the surfactant(s).

In one example, the concentration of Span-85 in the filler fluid phase is about 0.05% by volume. In yet another example, the concentration of Triton® X-15 in the filler fluid phase is in the range of about 0.05% to about 0.1% by volume. In yet another example, the concentration of Triton® X-15 in the filler fluid phase is about 0.2% by volume.

In another embodiment when the filler fluid phase additive includes Triton X-15. The concentration of Triton X-15 in the filler fluid phase may, for example, be in the range of from about 0.001% to about 0.3% by volume, or from about 0.005% to about 0.2% by volume, or from about 0.05% to about 0.2% by volume.

An important class of additives for use in the filler fluid phase is oil soluble fluorinated surfactants. A comprehensive list of fluorinated surfactants is available in Chapter 1 "Fluorinated Surfactants and Repellents" By Erik Kissa, Published by CRC Press, 2001, the entire disclosure of which is incorporated herein by reference.

In other embodiment, the filler fluid phase additive includes surfactants with oleophilic & hydrophilic groups. The oleophilic groups may, for example, be hydrocarbon or silicone based. In one embodiment, the surfactant has an HLB which is less than about 5 and a small hydrophilic group. In another embodiment, the surfactant has a long hydrophobic (oleophilic) chains, e.g., polymeric surfactants, such as silicone polymeric surfactants.

In yet another embodiment, the surfactants include oleophobic, oleophilic and hydrophilic groups. For example, the oleophobic groups may include fluorinated groups. The oleophilic groups may include hydrocarbon/silicone groups. In one embodiment, the surfactant has a short or low mw hydrophilic group. In another embodiment, the surfactant has a short or low mw fluorinated group. In one embodiment, the surfactant has a short or low mw hydrophilic group and a long or high mw hydrophobic or oleophilic group. In yet another embodiment, the surfactant has a short or low mw fluorinated group and a long or high mw hydrophobic or oleophilic group. In certain embodiments, such as semifluorinated alkanes, the surfactant may lack a hydrophilic group. Further, certain surfactants suitable for use in the present invention lack a hydrophilic group and include a short fluorinated group or a short fluorinated group with a long hydrophobic group. As described herein, short fluorines have generally 20 or less, 15 or less, or 10 or less fluorinated groups (eg —CF2— or CF3-). In one embodiment, the surfactant is a fluorosilicone.

Silicone surfactants may be used as filler fluid additives in accordance with the invention. Examples include DBE-224, DBE-621, and ABP-263, manufactured by Gelest.

Hydrocarbon surfactants are also suitable additives for the filler fluid phase. Examples include Tetronic 701, Tetronic 901, Tetronic 70R2, Tetronic 150R4, Tetronic 110R1, Tetronic 1301, Tetronic 150R1, Tetronix 1502, Pluronic 25R1, Pluronic L101, Pluronic L61, Pluronic L81, Plurafac A-24, by BASF; IGEPAL CA-210 and IGEPAL CO-210 by GEF; and SPAN 60, SPAN 65, SPAN 80, SPAN 85, ARLACEL 60, ARLACEL 83, BRIJ 52, BRIJ 93, ATMUL 500, ARSURF 2802, by ICI.

Fluorinated surfactants are also useful as additives to the filler fluid phase, e.g., PolyFox PF-636, 6320, 656, 6520, 651, 652 by Omnova; Masurf FS-910, FS-1400, FS-1900 by Mason Chemical Company; FC-4432 by 3M; FMS-141, FMS-736, FMS-121 (all examples of fluorosilicones) by Gelest; Zonyl 8857 and Zonyl FTS by Dupont; and fluorinated surfactants without hydrophilic groups.

A fluorinated oil based filler fluid may include a fluorinated oil soluble additive in the filler fluid. The oil soluble additive may be selected for reducing loss of target droplet phase components from the droplet. The oil soluble additive may comprise a nonionic low HLB (hydrophile-lipophile balance) surfactant. The HLB may be less than about 10, or less than about 5, or may range from about 2 to about 10, or may range from about 2 to about 9, or may range from about 2 to about 8, or may range from about 2 to about 7, or may range from about 2 to about 6, or may range from about 2 to about 5, or may range from about 3 to about 10, or may range from about 3 to about 9, or may range from about 3 to about 8, or may range from about 3 to about 7, or may range from about 3 to about 6, or may range from about 3 to about 5, or may range from about 4 to about 10, or may range from about 4 to about 9, or may range from about 4 to about 8, or may range from about 4 to about 7, or may range ranges from about 4 to about 6, or may range from about 4 to about 5. The oil soluble additive may present in an amount ranging from about 0.001% to about 0.3% by volume, or may range from about 0.005% to about 0.2% by volume, or may range from about 0.05% to about 0.2% by volume. The oil soluble additive comprises an oil soluble fluorinated surfactant. The oil soluble additive may comprise oleophilic and hydrophilic groups. The oil soluble additive may comprise a hydrocarbon or silicone oleophilic group. The oil soluble additive may comprise one or more fluorinated groups. The oil soluble additive may be selected from the group consisting of: Tetronic 701, Tetronic 901, Tetronic 70R2, Tetronic 150R4, Tetronic 110R1, Tetronic 1301, Tetronic 150R1, Tetronix 1502, Pluronic 25R1, Pluronic L101, Pluronic L61, Pluronic L81, Plurafac A-24, by BASF; IGEPAL CA-210 and IGEPAL CO-210 by GEF; and SPAN 60, SPAN 65, SPAN 80, SPAN 85, ARLACEL 60, ARLACEL 83, BRIJ 52, BRIJ 93, ATMUL 500, ARSURF 2802, by ICI. The oil soluble additive may be selected from the group consisting of: PolyFox PF-636, 6320, 656, 6520, 651, 652; Masurf FS-910, FS-1400, FS-1900; FC-4432 by 3M; FMS-141, FMS-736, FMS-121; Zonyl 8857 and Zonyl FTS.

7.2.1 Combinations of Surfactants

Combinations of surfactants may be used as droplet phase additives in accordance with the invention. Many droplet operations scenarios essentially have conflicting interfacial tension requirements. For example, while large-volume dispensing from a 2 mm dia opening is ideally conducted using a low interfacial tension, transport of droplets without tailing, hyperstability of droplets in the reservoir and bead handling are all best conducted using a moderate-to-large interfacial tension. Often, handling biological samples with a high protein load also imposes additional requirements on the surfactant solubility and HLB values.

In one embodiment of the invention, multiple surfactants are combined to satisfy different interfacial tension requirements for a particular application. For example, Span 85 is useful for selectively reducing the surface tension of oil, Triton X15 is useful for covering the droplet phase/filler fluid interface and thus preventing proteins from accumulating at the interface. Span 85 can be combined with very small quantities of Span 80 or a polymeric surfactant that can accumulate at the droplet phase/filler fluid interface and mimic the Triton X15 property, but still rendering a low oil surface tension. In one embodiment, the invention provides a filler fluid doped with a first surfactant having an HLB that is less than about 2 and a second surfactant having an HLB that is between about 2 and about 5. In another embodiment, the first surfactant forms forming the major proportion of surfactant and the second surfactant is included in trace quantities.

7.3 Changing pH to Adjust Solubility

The invention includes a droplet actuator having a droplet thereon having a target substance therein, where the droplet has a pH which has been adjusted away from the isoelectric point of the target substance in order to increase the solubility of the target substance. Similarly, the invention provides a method for preparing a fluid for conducting one of more droplet operations on a droplet actuator, where the method comprises adjusting the pH of the fluid in a direction which is away from the isoelectric point of the target substance in order to increase the solubility of the target substance. The adjustment may, for example, be achieved by combining the droplet with another droplet having a different pH. The invention further includes methods of conducting droplet operations, where the droplet operations are conducted using a droplet in which the pH has been adjusted as described here. The droplet having the adjusted pH may be wholly or partially surrounded by a filler fluid while present on the droplet actuator and/or while undergoing droplet operations.

Another aspect of the invention relates to changing the pH of a droplet in order to increase retention of a target substance in the droplet. For example, a first droplet having a target substance and a first pH may be combined with a second droplet having a second pH which is different from the first pH. When the first droplet and second droplet are combined using one or more droplet operations, the resulting combined droplet has a pH which is adjusted relative to the pH of the first droplet. In one aspect of the invention, the pH of the second droplet is selected so that the pH of the first droplet will be adjusted in a direction which is which is away from the isoelectric point of the target substance.

7.4 Filler Fluid Zones

The invention also provides an embodiment in which a single chip includes multiple oil zones. For example, different zones may have different additives or different surfactants or surfactant concentrations. Each zone may be loaded with an appropriate filler fluid formulation (surfactant concentration, viscosity, etc) to assist with droplet operations and other functions that are to occur within that zone. The zones may be separated by physical barriers, such as strips of gasket. For example, different parts of the assay protocol occur in each zone: the filler fluid in a washing zone may be doped with a higher concentration of surfactant to assist wash buffer loading from large off-chip wells; the filler fluid in the detection zone may have a reduced amount of surfactant to assist in transport of double droplets using a single electrode. An opening in the barriers may be associated with an electrode path for transporting droplets from one barrier to another. Filler fluids may mix through the openings so long as the mixing is not sufficient to eliminate the benefits conferred by the tailored zones.

The droplet actuator layout is scalable, such that a droplet actuator may include a few as one filler fluid zone up to tens, hundreds or more filler fluid zones.

In some cases, filler fluids may be selected with appropriate properties to prevent mixing between the filler fluids in different zones. For example, a fluorinated oil may be provided in a middle zone between two non-fluorinated oils.

In one specific embodiment, the invention provides a PCR chip with base fluid that is generally used throughout the droplet actuator except in heated locations where the temperature would be unduly detrimental to droplet operations using the base fluid; and a heat stable filler fluid that is used in heated locations where the temperature would be unduly detrimental to electowetting function using the base fluid. For example, in one embodiment, 2.0 cSt Silicone oil is used as the base oil and hexadacane is used in regions that are sufficiently heated to be unduly detrimental to electowetting function with the silicone oil.

In another embodiment, the opening in a barrier between zones may be sealed with a wax plug. In operation, when sufficient heat is applied, the wax melts. The wax droplet may be immiscible with the surrounding filler fluid and may be transported away from the opening. The wax droplet may be transported into the using droplet operations and cooled to seal the opening.

7.5 Heating Elements

In general, thermal control may be provided in three ways: (1) thermal control of the entire droplet actuator; (2) thermal control of a region of a droplet actuator using a heater that is in contact with or in proximity to the controlled region; and (3) thermal control of a region of the droplet actuator or the entire droplet actuator using a heater that is integrated into the droplet actuator (e.g., in the substrate comprising the path or array of electrodes and/or in a top substrate of the droplet actuator, when present). Combinations of the foregoing approaches are also possible.

In an integrated heater approach, temperature zones can be created and controlled using thermal control systems directly integrated into the droplet actuator. Thermal control elements (heating and/or cooling) may be integrated on the bottom substrate and/or top substrate (when present) of the droplet actuator and on the bottom and/or top surface of either substrate, or integrated within the structure of either substrate, or arranged between substrates. In one embodiment, the heating element is located in the barrier between filler fluid zones.

Each filler fluid zone may include distinct heating elements and may thus serve as a distinct thermal zone within the droplet actuator. This arrangement permits multiple steps in an analysis, such as sample preparation and thermal cycling, requiring different temperatures to be performed simultaneously at different temperatures in different filler fluid zones on a droplet actuator. For example, droplets can be physically transported or shuttled between filler fluid zones of different fixed temperatures to perform thermal cycling for an amplification reaction.

In one embodiment, heaters in the filler fluid zones may be formed using thin conductive films. Examples of suitable thin films include Pt heater wires and transparent indium-tin-oxide (ITO). In one embodiment, tiny metal (e.g., copper) vias in the PCB substrate are used to create tight thermal junctions between the liquid and the remote TC. An external thermocouple (TC) for temperature regulation can also be used to control temperature in a filler fluid zone.

7.6 Droplet Actuator Structure with Surfactant Layers

Key parameters for maintaining the stability of the oil film in a droplet actuator include interfacial tension between the oil film (i.e., oil phase) and the surface of the droplet actuator (i.e., solid phase), and interfacial tension between liquid (i.e., aqueous phase) and the surface of the droplet actuator, the viscosity of the oil phase, the applied voltage, and the size of the gap between the top and bottom substrates of the droplet actuator.

FIG. 1 illustrates a side view of a portion of a droplet actuator 100, showing an oil film between the droplet and the surfaces of the droplet actuator. Droplet actuator 100 may include a bottom substrate 110 that is separated from a top substrate 114 by a gap 118. A set of droplet operations electrodes 116, e.g., electrowetting electrodes, are arranged, for example, on bottom substrate 110. The droplet operations electrodes 116 are arranged for conducting droplet operations.

A hydrophobic layer 120 is disposed on the surface of bottom substrate 110 that is facing gap 118 (i.e., atop droplet operations electrodes 116). Similarly, another hydrophobic layer 120 is disposed on the surface of top substrate 114 that is facing gap 118. Hydrophobic layer 120 may be formed of, for example, a fluorinated hydrophobic coating, a hydrocarbon coating, a silicone coating, and/or an organic hydrophobic coating. Hydrophobic layer 120 has an affinity for an oil filler fluid 132 that is in gap 118. Hydrophobic layer 120 repels aqueous liquids, such as aqueous droplets that may be present along gap 118.

In one example, a droplet 128 may be present in gap 118 of droplet actuator 100. Droplet 128 may, for example, be a droplet of sample fluid or a reagent. Oil filler fluid 132 may, for example, be low-viscosity oil, such as silicone oil. Oil filler fluid 132 fills gap 118 and surrounds droplet 128. As droplet 128 moves along gap 118, an oil film 134 of oil filler fluid 132 forms between droplet 128 and the surfaces of droplet actuator 100. The stability of oil film 134 of oil filler fluid 132 that separates droplet 128 from hydrophobic layers 120 is important for optimum operation of droplet actuator 100. The stability of oil film 134 may be increased, for example, by decreasing the interfacial tension between oil filler fluid 132 and the surfaces within droplet actuator 100. In one embodiment, interfacial tension between oil filler fluid 132 (oil phase) and the surfaces within droplet actuator 100 (solid phase) may be modified by the addition of a surfactant to the oil filler fluid 132 within droplet actuator 100. An example of a droplet actuator that has additional filler fluid is described in more detail in FIGS. 2A and 2B.

Figure 2:
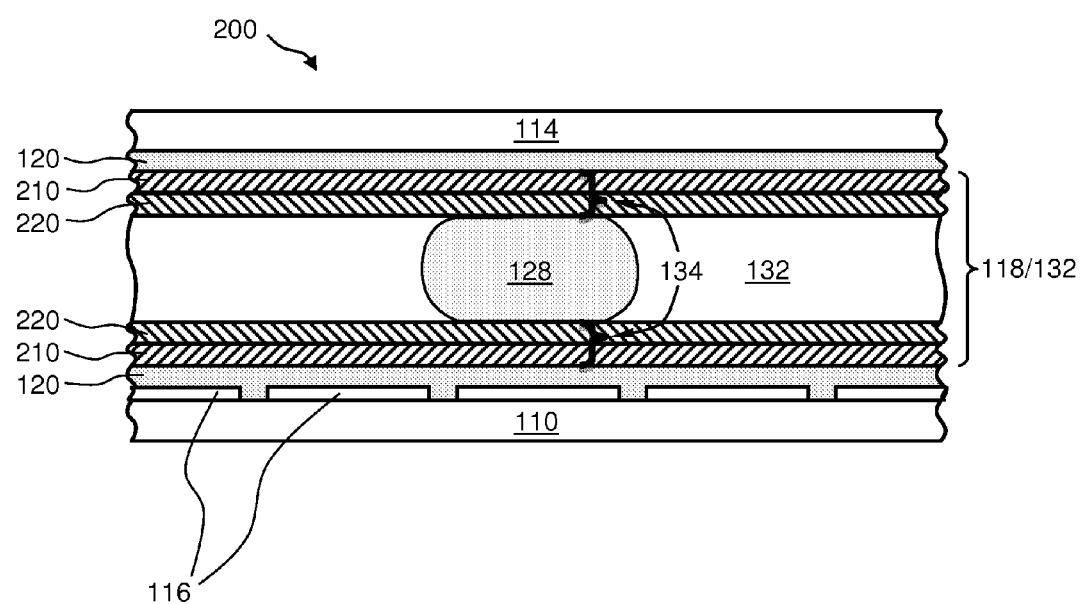
FIG. 2 illustrates a side view of a portion of a droplet actuator that includes layered filler fluids for assisting to maintain the stability of the oil film.

FIG. 2 illustrate side views of a portion of a droplet actuator 200 that includes filler fluid 132 including multilayered surfactants 210 and 220 for improving the stability of oil film 132. Droplet actuator 200 is substantially the same as droplet actuator 100 of FIG. 1, except that surfactant layers 210 and 220 are illustrated within filler fluid 132. Surfactant layers 210 and 220 may improve stability of the oil film 134. Thicknesses of the surfactant layers 210 and 220 are not to scale. Top substrate 114 and top surfactant layers 210 and 210 are illustrated, but are not required. Filler fluid 132 substantially fills gap 118, but complete filling of the gap with filler fluid 132 is not required.

In one embodiment, filler fluid 132 may include first surfactant layer 210 and a second surfactant layer 132. First surfactant layer 210 may be generally oriented atop hydrophobic layer 120. Second surfactant layer 132 may be generally oriented atop first surfactant layer 210. It will be appreciated that in addition to the layers illustrated, some portion of one or both surfactants may be distributed elsewhere in filler fluid 132. Droplet 128 provides an aqueous phase for conducting droplet operations mediated by electrodes 116. Droplet 128 may be partially surrounded by filler fluid 132. Alternatively, droplet 128 may be substantially surrounded by filler fluid 132.

In one embodiment, hydrophobic layer 120 includes a fluorinated hydrophobic coating. In a related embodiment, hydrophobic layer 120 includes a fluorinated hydrophobic coating and first surfactant 210 includes a fluorinated oil. In another related embodiment, hydrophobic layer 120 includes a fluorinated hydrophobic coating, first surfactant 210 includes a fluorinated surfactant, and second surfactant 220 includes an oleophilic oil.

In another embodiment, hydrophobic layer 120 includes a hydrocarbon, a silicone, and/or an organic hydrophobic coating. In a related embodiment, hydrophobic layer 120 includes a hydrocarbon, a silicone, and/or an organic hydrophobic coating and first surfactant 210 includes fluorinated surafactant. In another related embodiment, hydrophobic layer 120 includes a hydrocarbon, a silicone, and/or an organic hydrophobic coating; surfactant 210 includes a fluorinated surfactant, and second surfactant 210 includes a fluorinated surfactant.

Examples of suitable oleophilic surfactants include, without limitation, sugar esters, such as sorbitan fatty acid esters (e.g., sorbitantrioleate, sorbitantrilaurate, sorbitantripalmitate, sorbitantristearate and sorbitantrisesquioleate) and sucrose fatty acid esters; glycerin fatty acid esters; and fatty acid monoglycerides.

Examples of suitable fluorinated surfactants include, without limitation, 1H,1H,2H,2H-perfluoro-1-decanol and 1H,1H,2H,2H-perfluoro-1-octanol; as well as perfluorinated surfactants, such as perfluorodecanoic acid and perfluorododecanoic acid. A list of fluorinated surfactants is available in Chapter 1 "Fluorinated Surfactants and Repellents" By Erik Kissa, Published by CRC Press, 2001, the entire disclosure of which is incorporated herein by reference. Other suitable fluorinated surfactants are described in Michael Terrazas & Rudi Dams, "A new generation of fluorosurfactants," Speciality Chemicals Magazine, March 2004, vol 24 no 3, the entire disclosure of which is incorporated herein by reference.

7.7 Filler Fluid Viscosity

The stability of the oil film may be increased by increasing the interfacial tension between droplet 128 (the aqueous phase) and hydrophobic layer 120 (the solid phase). In one embodiment, the invention comprises selecting an oil filler fluid having sufficiently high viscosity to maintain the integrity of the oil film during the conduct of one or more droplet operations.

7.8 Gap Height

Increasing the size of gap 118, i.e., the distance between bottom substrate 110 and top substrate 114, results in a decrease in the interfacial tension between the oil phase and solid phase, which increases the stability of the oil film. The invention may comprise selecting a gap height which is sufficiently large relative to the unit droplet size to maintain the integrity of the oil film during the conduct of one or more droplet operations. The unit droplet size is roughly the size of a droplet operations electrode. In one embodiment, top substrate 114 may be omitted altogether.

7.9 Droplet Actuator Structure with Barriers

Lengthy electrode activation may be detrimental to oil film stability. Consequently, it may be useful in some cases to minimize the length of time that an electrode is activated. Current techniques activate an electrode to move a droplet into place atop the electrode and to retain the droplet in place. The invention includes a technique whereby electrode activation is used to move a droplet into place, while physical barriers are used to retain the droplet in place. In this manner, the duration of electrode activation may be limited to the duration necessary to move the droplet into place.

Figure 3:
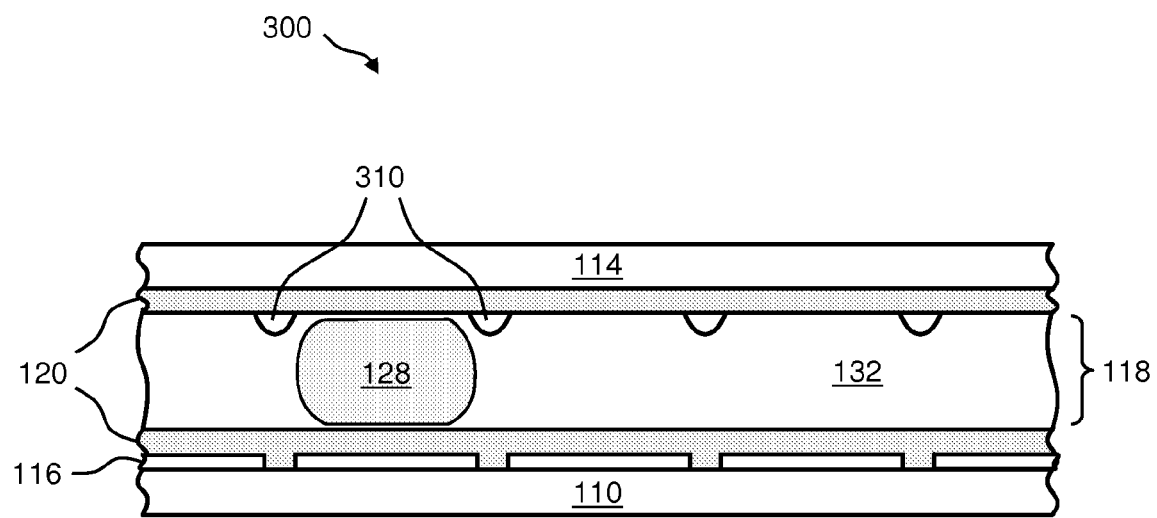
FIG. 3 illustrates a side view of a portion of a droplet actuator that includes physical structures for droplet retention.

FIG. 3 illustrates a side view of a portion of a droplet actuator 300 that includes physical structures for droplet retention. Droplet actuator 300 may be substantially the same as droplet actuator 100 of FIG. 1, except for the inclusion of barriers 310 on, for example, the surface of top substrate 114 that is facing gap 118. Barriers 310 may be physical structures that are placed approximately at the edges of or between droplet operations electrodes 116. Barriers 310 may be formed by, for example, embossing. Barriers 310 are designed to permit droplet transport, while at the same time hinder droplet drift in the absence of an activated electrode. Other types of physical features may be used so long as they permit droplet transport, while at the same time hinder droplet drift in the absence of an activated electrode.

In operation, droplet operations electrodes 116 of droplet actuator 300 may be activated to transport droplet 128. Subsequent to transport of droplet 128, droplet operations electrode 116 may be deactivated. Droplet 128 is then prevented by barriers 310 from drifting away from droplet operations electrode 116. Barriers 310 are provided in order to retain droplet 128 on a certain droplet operations electrode 116 even in the absence of an applied electrowetting voltage. As a result, the presence of barriers 310 allows the applied electrowetting voltage to be removed and/or reduced upon completion of the droplet operations, thereby helping to maintain the stability of the oil film.

7.10 Adjustable Electrowetting Voltages in a Droplet Actuator

Modulating the voltage used to perform droplet operations may assist in maintaining the stability of the oil film. In general, minimizing the voltage level of the electrowetting voltage and/or the duration that the voltage is applied during droplet operations may be beneficial for maintaining the stability of the oil film.

Embodiments of the invention may utilize certain feedback mechanisms for monitoring droplet operations and adjusting the electrowetting voltage accordingly. Using substantially continuous feedback mechanisms permits voltage duration to be reduced to the duration necessary to carry out a certain droplet operation. In one example, capacitance detection may be used as the substantially continuous feedback mechanism. Examples of capacitance feedback mechanisms suitable for use in the present invention are described in International Patent Application No. PCT/US08/54134, entitled "Capacitance Detection in a Droplet Microactuator," filed on Feb. 15, 2008, the entire disclosure of which is incorporated herein by reference. In another example, an optical feedback system, such as a camera in combination with image processing technologies, may be used as the substantially continuous feedback mechanism. Examples of using adjustable electrowetting voltages to help maintain the stability of the oil film are described with reference to FIGS. 4A, 4B, 4C, and 5.

Figure 4A:
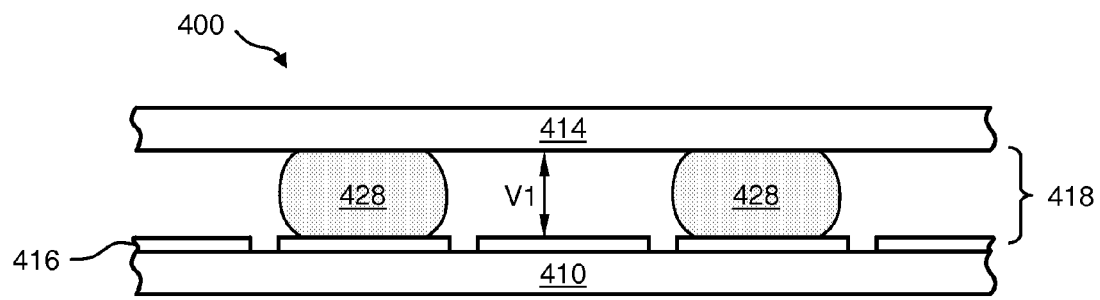
FIG. 4A illustrates a side view of a portion of a droplet actuator that includes a droplet transport region that requires a certain electrowetting voltage for transporting droplets.

FIG. 4A illustrates a side view of a portion of a droplet actuator 400. This portion of droplet actuator 400 includes a droplet transport region that requires a certain electrowetting voltage for transporting droplets. Droplet actuator 400 may include a bottom substrate 410. Bottom substrate 410 may be separated from a top substrate 414 by a gap 418. The transport region of droplet actuator 400 may include a line or path of droplet operations electrodes 416 (e.g., electrowetting electrodes) that may be associated with bottom substrate 410. One or more droplets 428 may be contained in gap 118 of droplet actuator 400. In order to transport droplets 428 along droplet operations electrodes 416, a certain electrowetting voltage is applied. For example, an electrowetting voltage V1 from about 125 volts to about 175 volts (e.g., about 150 volts) may be sufficient for transporting droplets along droplet operations electrodes 416.

Figure 4B:
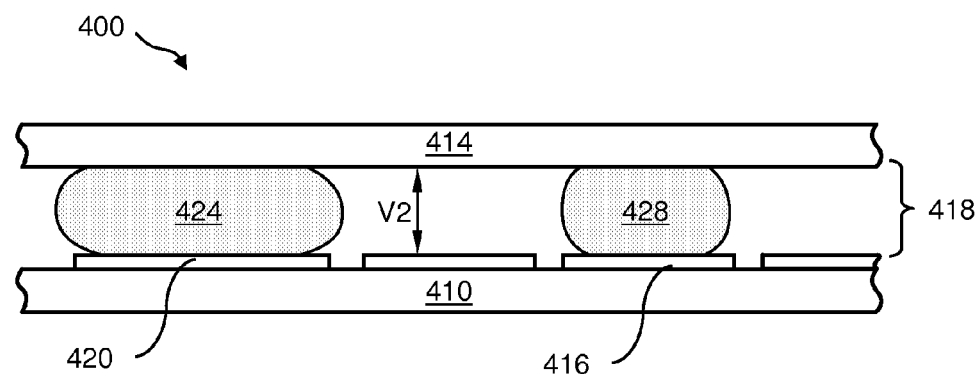
FIG. 4B illustrates a side view of another portion of the droplet actuator of FIG. 4A that includes an on-chip reservoir that requires a certain electrowetting voltage for dispensing droplets.

FIG. 4B illustrates a side view of another portion of droplet actuator 400. This portion of droplet actuator 400 includes an on-chip reservoir that requires a certain electrowetting voltage for dispensing droplets. An on-chip reservoir electrode 420 may be disposed on bottom substrate 410. On-chip reservoir electrode 420 may be arranged in association with the line or path of droplet operations electrodes 416. On-chip reservoir electrode 420 is illustrated as being larger than droplet operations electrodes 416, but may be the same size or smaller. In some cases, on-chip reservoir electrode 420 is simply replaced with another droplet operations electrode 416.

Droplets may be dispensed from on-chip reservoir electrode 420 onto the droplet operations electrodes 416. More specifically, a volume of sample fluid 424 is provided at on-chip reservoir electrode 420. Droplets, such as a droplet 428, may be dispensed from sample fluid 424 by applying a certain electrowetting voltage. For example, an electrowetting voltage V2 from about 150 volts to about 200 volts (e.g., about 175 volts) may be sufficient for dispensing droplets from on-chip reservoir electrode 420.

Figure 4C:
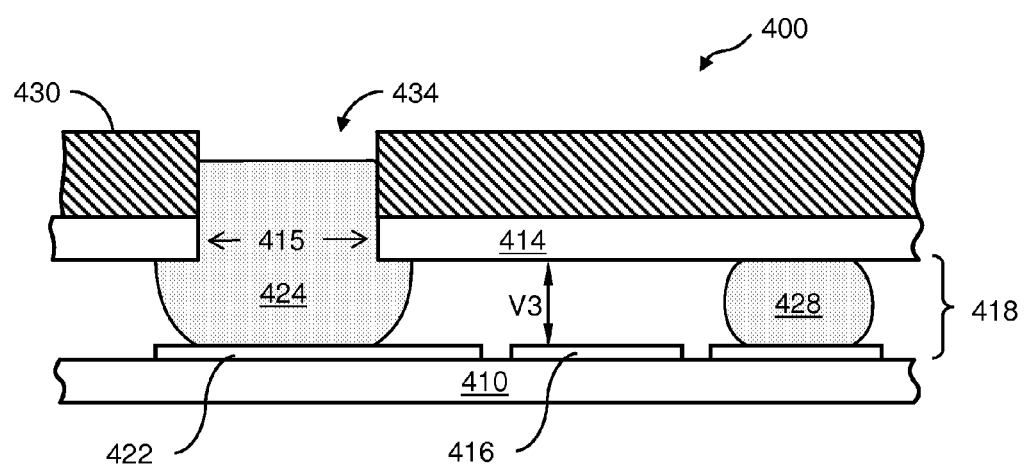
FIG. 4C illustrates a side view of yet another portion of the droplet actuator of FIG. 4A that includes an off-chip reservoir that requires yet another certain electrowetting voltage for dispensing droplets.

FIG. 4C illustrates a side view of yet another portion of droplet actuator 400. This portion of droplet actuator 400 includes an off-chip reservoir that requires yet another electrowetting voltage for dispensing droplets. A substrate 420, such a plastic substrate, is mounted atop top substrate 414. Substrate 420 includes a well 434 for holding a volume of fluid 424. Well 434 is substantially aligned with an opening 415 in top substrate 414. Additionally, the opening in top substrate 414 is substantially aligned with an reservoir electrode 422, which may be disposed on bottom substrate 410. Reservoir electrode 422 may be arranged in sufficient proximity to one or more electrodes in the line or path of droplet operations electrodes 416 such that the one or more electrodes may be used to conduct one or more droplet operations using fluid 424 introduced into gap 418 via opening 415. Reservoir electrode 422 is illustrated as being larger than droplet operations electrodes 416, but may be the same size or smaller. In some cases, reservoir electrode 422 is simply replaced with another droplet operations electrode 416. The fluid path from well 434 into gap 418 permits reservoir electrode 422 to interact with fluid 424. Fluid 424 may, for example, be a wash fluid or a sample fluid.

In this example, wash droplets may be dispensed from reservoir electrode 422 onto the droplet operations electrode 416. More specifically, a volume of fluid 424 is provided at reservoir electrode 422. Droplets 428, which may be wash droplets, may be dispensed from fluid 424 by applying a certain electrowetting voltage. For example, an electrowetting voltage V3 from about 200 volts to about 250 volts (e.g., about 225 volts) may be sufficient for dispensing droplets from reservoir electrode 422.

Referring to FIGS. 4A, 4B, and 4C, a higher voltage may be required to pull fluid into the gap and to subsequently dispense droplets from an reservoir electrode (e.g., V3 of FIG. 3C) as compared with an on-chip reservoir electrode (e.g., V2 of FIG. 3B), and as compared to the droplet transport operations (e.g., V1 of FIG. 3A). In another example, even lower voltages (e.g., V0) than the voltage V1 that is sufficient for droplet transport may be required to prevent droplet drift (i.e., keeping a droplet in place). Voltage requirements for the different droplet operations of droplet actuator 400 may be described as $V0 \leq V1 \leq V2 \leq V3$. FIGS. 4A, 4B, and 4C describe examples wherein different voltage levels may be just sufficient (and with just sufficient time) to perform the certain droplet operations, which may be beneficial for maintaining the stability of the oil film. In one embodiment, the invention provides a droplet actuator configured for applying a voltage to each electrode, wherein the voltage applied to each electrode is selected to be optimized for the specific task being conducted by the electrode. In one such embodiment, the voltages applied are $V0 \leq V1 \leq V2 \leq V3$, as described above.

Figure 5:
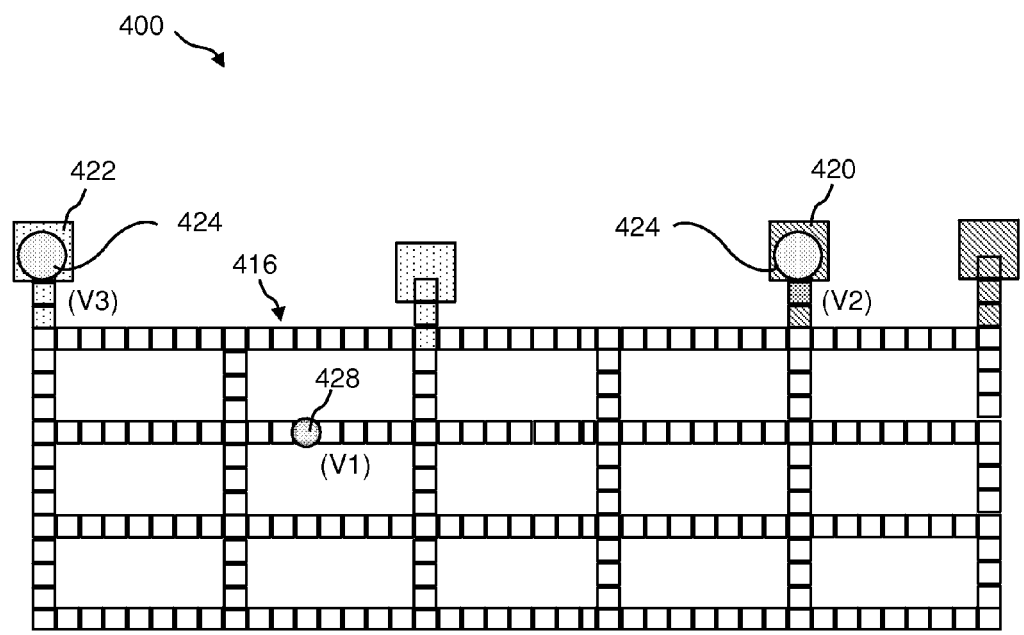
FIG. 5 illustrates a top view of the droplet actuator of FIGS. 4A, 4B, and 4C and shows the different regions therein that may require different voltages.

FIG. 5 illustrates a top view of droplet actuator 400 that is described in FIGS. 4A, 4B, and 4C and illustrates regions that may require different voltages. For example, FIG. 5 shows multiple lines or paths of droplet operations electrodes 416 along which droplets, such as droplet 428, may be transported using, for example, electrowetting voltage V1. Additionally, on-chip reservoir electrode 420 is shown, from which droplets may be dispensed using, for example, electrowetting voltage V2. Further, reservoir electrode 422 is shown, from which droplets may be dispensed using, for example, electrowetting voltage V3. Feedback mechanisms (not shown), such as capacitance detection and optical detection mechanisms, may be associated with droplet actuator 400 for monitoring droplet operations. By monitoring the droplet operations in a substantially continuous manner, the electrowetting voltage levels, the amount of time for applying the voltage levels, the voltage shape (i.e., waveform), location at which to apply the voltage, and so on, may be determined and controlled. For example, the minimum voltage and duration may be applied to perform a transport operation. Then, once it has been determined that the transport operation is complete, the voltage may be reduced or removed.

In one embodiment, different voltages may be applied to droplets having different functions. For example, when transporting a sample droplet, smaller or minimum voltages and voltage durations may be used to reduce contamination of the droplet actuator surface. Subsequent cleaning droplets may be transported using higher voltages in order to maximize contact of the cleaning droplet with the droplet actuator surface. In other words, in some cases, disrupting the oil film may be useful, particularly for clean-up purposes. It may also be useful to disrupt the oil film for depositing substances on a surface of the droplet actuator. The oil film may be disrupted by increasing voltage and/or voltage time. Further, the sample droplet may be followed by a low interfacial tension cleaning droplet so that whatever rupture in the oil film that the sample droplet may have caused is restored by the cleaning droplet, which picks up the contamination. In this example, the cleaning droplet has about the same characteristics as the sample droplet and, therefore, uses about the same voltage.

7.11 Droplet Phase Fluids

For examples of fluids that may be subjected to droplet operations using the approach of the invention, see the patents listed in section 2, especially International Patent Application No. PCT/US2006/047486, entitled, "Droplet-Based Biochemistry," filed on Dec. 11, 2006. In some embodiments, the fluid includes a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, fluidized tissues, fluidized organisms, biological swabs and biological washes. In some embodiment, the fluid includes a reagent, such as water, deionized water, saline solutions, acidic solutions, basic solutions, detergent solutions and/or buffers. In some embodiments, the fluid includes a reagent, such as a reagent for a biochemical protocol, such as a nucleic acid amplification protocol, an affinity-based assay protocol, a sequencing protocol, and/or a protocol for analyses of biological fluids.

The fluids may include one or more magnetically responsive and/or non-magnetically responsive beads. Examples of droplet actuator techniques for immobilizing magnetic beads and/or non-magnetic beads are described in the foregoing international patent applications and in Sista, et al., U.S. Patent Application No. 60/900,653, entitled "Immobilization of Magnetically-responsive Beads During Droplet Operations," filed on Feb. 9, 2007; Sista et al., U.S. Patent Application No. 60/969,736, entitled "Droplet Actuator Assay Improvements," filed on Sep. 4, 2007; and Allen et al., U.S. Patent Application No. 60/957,717, entitled "Bead Washing Using Physical Barriers," filed on Aug. 24, 2007, the entire disclosures of which is incorporated herein by reference.

8 CONCLUDING REMARKS

The foregoing detailed description of embodiments refers to the accompanying drawings, which illustrate specific embodiments of the invention. Other embodiments having different structures and operations do not depart from the scope of the present invention. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

We claim:

1. A droplet actuator comprising:
   (a) two substrates separated to form a droplet operations gap, one or both of the substrates comprising electrodes arranged to conduct electrowetting droplet operations, the electrodes underlying a hydrophobic coating;
   (b) multiple oil zones in the gap, each such oil zone comprising an oil filler fluid having a formulation which is different oil filler fluid formulations of other oil zones, at least one such oil zone comprising a fluorinated oil based filler fluid comprising a fluorinated oil soluble additive in the filler fluid, and wherein the electrodes are arranged to conduct electrowetting mediated droplet operations transporting droplets from one oil zone to another oil zone; and
   (c) a droplet in contact with the oil filler fluid of at least one of the multiple oil zones, wherein the droplet is subject to electrowetting droplet operations mediated by the electrodes, including electrowetting mediated droplet operations transporting the droplet from one oil zone to another oil zone.

2. The droplet actuator of claim 1 wherein the fluorinated oil soluble additive is selected for reducing loss of target droplet phase components from the droplet.

3. The droplet actuator of claim 1 wherein the fluorinated oil soluble additive comprises a nonionic low HLB (hydrophile-lipophile balance) surfactant.

4. The droplet actuator of claim 3 wherein the HLB is less than about 10.

5. The droplet actuator of claim 3 wherein the HLB is less than about 5.

6. The droplet actuator of claim 3 wherein the HLB ranges from about 2 to about 10.

7. The droplet actuator of claim 3 wherein the HLB ranges from about 2 to about 9.

8. The droplet actuator of claim 3 wherein the HLB ranges from about 2 to about 8.

9. The droplet actuator of claim 3 wherein the HLB ranges from about 2 to about 7.

10. The droplet actuator of claim 3 wherein the HLB ranges from about 2 to about 6.

11. The droplet actuator of claim 3 wherein the HLB ranges from about 2 to about 5.

12. The droplet actuator of claim 3 wherein the HLB ranges from about 3 to about 10.

13. The droplet actuator of claim 3 wherein the HLB ranges from about 3 to about 9.

14. The droplet actuator of claim 3 wherein the HLB ranges from about 3 to about 8.

15. The droplet actuator of claim 3 wherein the HLB ranges from about 3 to about 7.

16. The droplet actuator of claim 3 wherein the HLB ranges from about 3 to about 6.

17. The droplet actuator of claim 3 wherein the HLB ranges from about 3 to about 5.

18. The droplet actuator of claim 3 wherein the HLB ranges from about 4 to about 10.

19. The droplet actuator of claim 3 wherein the HLB ranges from about 4 to about 9.

20. The droplet actuator of claim 3 wherein the HLB ranges from about 4 to about 8.

21. The droplet actuator of claim 3 wherein the HLB ranges from about 4 to about 7.

22. The droplet actuator of claim 3 wherein the HLB ranges from about 4 to about 6.

23. The droplet actuator of claim 3 wherein the HLB ranges from about 4 to about 5.

24. The droplet actuator of claim 1 wherein the fluorinated oil soluble additive is present in an amount ranging from about 0.001% to about 0.3% by volume.

25. The droplet actuator of claim 1 wherein the fluorinated oil soluble additive is present in an amount ranging from about 0.005% to about 0.2% by volume.

26. The droplet actuator of claim 1 wherein the fluorinated oil soluble additive is present in an amount ranging from about 0.05% to about 0.2% by volume.

27. The droplet actuator of claim 1 wherein the fluorinated oil soluble additive comprises an oil soluble fluorinated surfactant.

28. The droplet actuator of claim 1 wherein the fluorinated oil soluble additive comprises oleophilic and hydrophilic groups.

29. The droplet actuator of claim 28 wherein the fluorinated oil soluble additive comprises a hydrocarbon or silicone oleophilic group.

30. The droplet actuator of claim 28 wherein the fluorinated oil soluble additive comprises one or more fluorinated groups.

31. The droplet actuator of claim 1 wherein the fluorinated oil soluble additive comprises an additive selected from the group consisting of: Tetronic 701, Tetronic 901, Tetronic 70R2, Tetronic 150R4, Tetronic 110R1, Tetronic 1301, Tetronic 150R1, Tetronix 1502, Pluronic 25R1, Pluronic L101, Pluronic L61, Pluronic L81, Plurafac A-24, by BASF; IGEPAL CA-210 and IGEPAL CO-210 by GEF; and SPAN 60, SPAN 65, SPAN 80, SPAN 85, ARLACEL 60, ARLACEL 83, BRIJ 52, BRIJ 93, ATMUL 500, ARSURF 2802, by ICI.

32. The droplet actuator of claim 1 wherein the fluorinated oil soluble additive comprises an additive selected from the group consisting of: PolyFox PF-636, 6320, 656, 6520, 651, 652; Masurf FS-910, FS-1400, FS-1900; FC-4432 by 3M; FMS-141, FMS-736, FMS-121; Zonyl 8857 and Zonyl FTS.

33. The droplet actuator of claim 1 wherein at least one of the oil zones comprises a heat stable oil.

34. The droplet actuator of claim 1 comprising one or more barriers between the oil zones, the barrier comprising an opening for transporting droplets from one zone to another.

35. The droplet actuator of claim 34 comprising one or more barriers between the oil zones, wherein the opening comprises a wax plug.

36. The droplet actuator of claim 1 wherein at least one of the zones comprises a non-fluorinated oil.

* * * * *